(12) United States Patent
Löper et al.

(10) Patent No.: US 10,954,507 B2
(45) Date of Patent: Mar. 23, 2021

(54) METHOD FOR ISOLATING RNA WITH HIGH YIELD

(71) Applicant: QIAGEN GMBH, Hilden (DE)

(72) Inventors: David Löper, Hilden (DE); Kerstin Steinert, Hilden (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 15/324,993

(22) PCT Filed: Jul. 17, 2015

(86) PCT No.: PCT/EP2015/066447
§ 371 (c)(1),
(2) Date: Jan. 9, 2017

(87) PCT Pub. No.: WO2016/009059
PCT Pub. Date: Jan. 21, 2016

(65) Prior Publication Data
US 2017/0198279 A1    Jul. 13, 2017

(30) Foreign Application Priority Data
Jul. 17, 2014   (EP) .................................... 14177538

(51) Int. Cl.
*C12N 15/10* (2006.01)
(52) U.S. Cl.
CPC ..... *C12N 15/1006* (2013.01); *C12N 15/1003* (2013.01)
(58) Field of Classification Search
None
See application file for complete search history.

(56) References Cited

U.S. PATENT DOCUMENTS

| 6,204,375 B1 | 3/2001 | Lader |
| 2010/0221788 A1 | 9/2010 | Radmarcher et al. |

FOREIGN PATENT DOCUMENTS

| EP | 2163622 A1 | 3/2010 |
| WO | WO 00/06780 | 2/2000 |
| WO | WO 2005/012523 A1 | 2/2005 |
| WO | WO 2005/054466 A2 | 6/2005 |

OTHER PUBLICATIONS

Chomczynski P. et al., "Single-Step Method of RNA Isolation by Acid Guanidinium Thiocyanate-Phenol-Chloroform Extraction," *Analytical Biochemestry*, 162:156-159,1987.
Cohn, E.J. et al., "A system for the Separation of the Components of Human Blood: Quantifative Procedures for the Separation of the Protein Components of Human Plasma [1] [a,b,c]" *J. Am. Chem. Soc.*, 72:465-474,1950.
Zaworski P.G. et al., "Precipitation and Recovery of Proteins from Culture Supernatants Using Zinc," *Analytical Biochemistry*, 173:440-444,1988.
Contributed by Rex E. Lovrien and Daumantas,"Matuliselective Precipitation of Proteins", *Current Protocols in Protein Science*, Unit 4.5:4.5.1.-4.5.36,1997.
EP Office Action issued in EP Appl. No. 15 742 208.0 dated Apr. 4, 2018.
English language translation of the Notice of Reasons for Rejection for Japanese Publ. No. 2017-502197, dated May 23, 2019.
Notice on the Second Office Action for CN Appl. No. 2015800389313, dated Aug. 8, 2019.

*Primary Examiner* — James Martinell
(74) *Attorney, Agent, or Firm* — Seyfarth Shaw LLP

(57) ABSTRACT

A phenol-free method for isolating a nucleic acid from a sample is provided, said method comprising the following steps: a) preparing a precipitation mixture by adding at least one metal cation precipitant and at least one organic solvent selected from aprotic polar solvents and protic solvents to the sample, wherein the precipitation mixture i) comprises the metal cation precipitant; ii) comprises the organic solvent in a concentration of 15% or less; iii) comprises a buffering agent; and iv) has an acidic pH value, and precipitating proteins; b) separating the precipitate from the supernatant, wherein the supernatant comprises small RNA having a length of less than 200 nt and large RNA having a length of at least 1000 nt; and c) isolating a nucleic acid from the supernatant. Using an organic solvent as claimed during the protein precipitation step in the defined concentration provides a supernatant which in addition to small RNA also comprises large RNA. This is an advantage as the present method provides more flexibility to the user. The described method can be used for isolating and hence analysing different target RNAs.

17 Claims, 14 Drawing Sheets

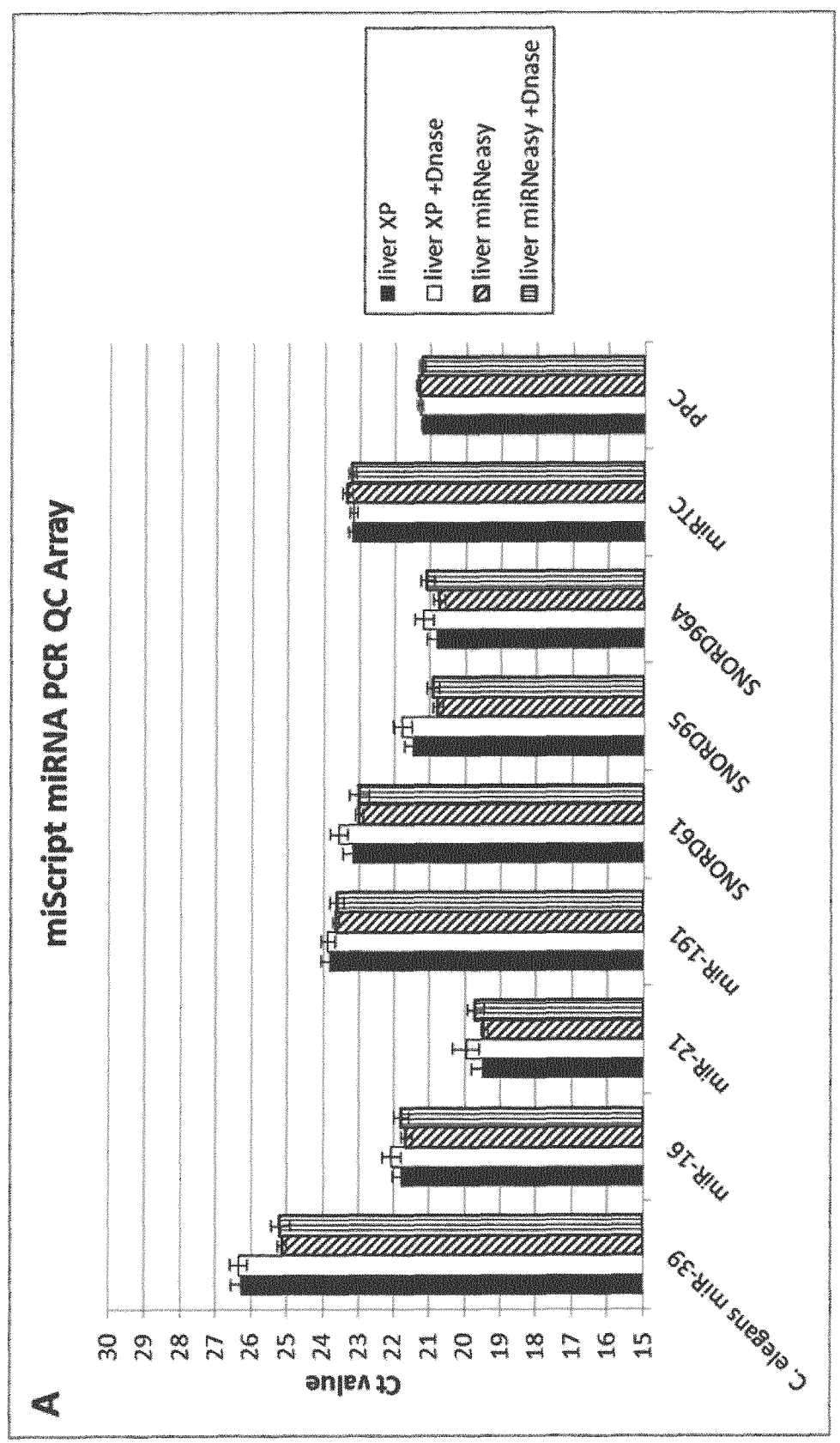

METHOD FOR ISOLATING RNA WITH HIGH YIELD

The present invention pertains to a method for isolating a nucleic acid such as RNA from a sample and in particular provides means for efficiently isolating small RNA and large RNA with high yield from various samples, including protein-rich samples by using a phenol-free RNA isolation method.

The study of small nucleic acids in the order of 200 nucleotides or less from various tissues, body fluids and other biological samples is an area of extreme interest and promises to remain one for the future. Small nucleic acids in particular include but are not limited to small RNAs such as inter alia micro RNAs (miRNA) and small interfering RNA molecules both of which can have a powerful effect on the expression of a gene. Furthermore, also other small nuclear and small nucleolar RNAs (e.g. snRNAs and snoRNAs) involved in mRNA and rRNA processing are of interest. Furthermore, nucleic acids such as RNA having a length of 500 nucleotides or less are also often contained as degradation products in other samples and must be efficiently captured therefrom. With the increasing interest in respective small RNAs, the standard isolation procedures have been modified to facilitate the isolation of small nucleic acids and to improve the yield of small nucleic acids. Such improvements were necessary because standard protocols used to isolate total RNA are usually not ideal for isolating small RNAs because small RNA is often not effectively bound using standard methods. Therefore, total RNA isolated using standard procedures usually does not comprise small RNA in sufficient amounts for a subsequent analysis. These low yields are attributable to that small RNAs are either not bound or get lost during the nucleic acid isolation procedure. Therefore, methods were developed that allow the efficient isolation of total RNA, which includes the desired small RNAs or which selectively isolate small RNA (without larger RNA) from the samples.

Common methods designed to isolate small RNA, such as in particular small, single-stranded RNA such as miRNAs, require rather high alcohol concentrations of ≥45% or preferably ≥50% during binding to ensure efficient binding of the small RNA to a nucleic acid binding solid phase. The binding efficiency increases with increasing alcohol concentration.

However, these high alcohol concentrations required to ensure efficient RNA binding to the solid phase cause problems which disturb the isolation procedure. In particular when processing protein-rich samples such as plasma, serum or tissue samples, the high alcohol concentration that is required during the RNA binding step can result in that proteins are precipitated. These precipitates are contaminants that disturb the isolation procedure, because they e.g. bind unspecifically to and thereby block the solid phase and/or are carried over as contaminants into the eluate.

Established methods for isolating small RNA from protein-rich samples therefore include a protein removal step prior to establishing the binding conditions that allow to bind small RNA.

Protein removal techniques include e.g. a phenol/chloroform extraction or a protein precipitation step. Other methods employ a time consuming enzymatic protein digestion step such as a digestion with proteinase K. Alternatively, the sample is heavily diluted or the alcohol concentration during binding is reduced which has the drawback that the isolation efficiency is reduced. The problems associated with these known methods are described subsequently in further detail.

Phenol/chloroform-based organic extraction methods are often performed according to the Chomczynski method (Chomczynski and Sacchi, 1987: Single-step method of RNA isolation by acid guanidinium thiocyanate-phenol-chloroform extraction. Anal. Biochem. (162): 156-159). According to said methods, the RNA is concentrated during phenol/chloroform extraction in the aqueous phase and is then subsequently isolated therefrom e.g. by adding alcohol to the aqueous phase and binding the RNA to a nucleic acid binding solid phase. In said RNA binding step, special conditions such as a high alcohol concentration are likewise required to efficiently bind and thus capture the small RNAs in the isolated total RNA. A commercial kit that is based on a respective phenol/chloroform method is the mirVana miRNA isolation kit (Ambion). After phenol/chloroform extraction, the protocol follows a fractionation strategy, wherein larger RNAs (more than 200 nucleotides) are bound in a first binding step to a nucleic acid binding solid phase at moderate alcohol concentrations (typically 25%). The flow-through comprises the small RNAs. Said small RNAs are captured from the flow-through by a second binding step wherein the alcohol concentration is raised to more than 50% (typically 55%) and the small RNA is bound to a second solid phase from which it can be eluted. Furthermore, a protocol is provided with the mirVana miRNA isolation kit wherein total RNA including small RNA is isolated from the aqueous phase that is obtained after the phenol/chloroform extraction. Here, the binding conditions are established by increasing the alcohol concentration to the required amounts to allow efficient binding of small RNA (typically 55%) in one step. Similar methods are also described in WO 2005/012523 and WO 2005/054466. However, also in these protocols an organic phenol/chloroform extraction step is usually performed in advance. Another phenol/chloroform based commercial product is the miRNeasy Mini kit (QIAGEN). It provides high quality and high yields of total RNA including small RNA from various different biological samples.

Generally, phenol based isolation procedures are relatively insensitive regarding the sample composition or the protein content. However, the sample is usually combined with 5 to 10 volumes of a phenol containing solution. This results in a relatively high sample volume that needs to be processed. Therefore, the initial sample volume is often rather small and lies in the range of 100 μl to 200 μl, seldom up to 500 μl. This is a disadvantage, in particular if the target small RNA is present in a low concentration in the initial sample. A further disadvantage is that phenol can be carried over into the eluate. Furthermore, each sample needs to be treated manually. Besides these technical difficulties and limitations, in particular the strong toxicity of phenol is perceived as disadvantage. Therefore, there is a great demand for phenol-free RNA isolation methods which allow to isolate total RNA including small RNA from various samples with high yield and quality.

Phenol-free methods for isolating RNA including small RNAs are also known in the prior art. To allow binding of total RNA including small RNA to a nucleic acid binding solid phase often a chaotropic salt and alcohol in a high concentration is used. Usually, the nucleic acid binding solid phase used comprises or consists of silica. However, the recovery of small RNA species like miRNA in methods that are based on binding the RNA to silica surfaces in the presence of alcohol and chaotropic substances require very high alcohol concentrations. Usually, approximately at least 50% alcohol is used in the binding mixture, usual ranges include 50-80% (v/v) alcohol in the binding mixture. However, when using respective phenol-free protocols that use high alcohol concentrations during binding, the total RNA yield and also the obtained small RNA yield is often reduced when processing protein-rich samples which could be a consequence of protein precipitations that are induced when alcohol is added in a high concentration to the disrupted sample. Some methods therefore limit the initial sample volume or reduce the alcohol concentration that is used during RNA binding (see above). Both measures allow to reduce the risk that the isolation is disturbed by precipitating proteins. However, the small nucleic acid isolation efficiency is reduced because binding is less efficient and/or the reduced input sample volume has the drawback that the overall concentration of small nucleic acids that can be isolated is reduced. Thus, generally, the performance of these protocols is unfortunately not comparable with phenol/chloroform based isolation methods. The problems are in particular observed with column based methods.

Other phenol-free methods include a protein precipitation step that is performed prior to the actual RNA isolation step. Protein precipitation is initiated by metal cations which is an established method for selectively precipitating proteins (see e.g. Lovrien, R. E. and Matulis, 2001 "Selective precipitation of proteins. Current Protocols in Proteins Science. 7:4.5.1-4.5.36). A respective method is described in EP 2 163 622. Here, the isolation of small RNA having a length of ≤200 nt from different sample types is disclosed. Metal cations are used to precipitate proteins and furthermore, larger nucleic acids are removed either prior to or during the protein precipitation step. The small RNA is then subsequently isolated from the obtained supernatant, by adding an organic solvent such as an apolar, protic organic solvent, e.g. THF, in a high concentration to the supernatant. This method selectively isolates small RNA, wherein the major amount of larger RNA (such as mRNA) and genomic DNA is lost and therefore, is not available for a subsequent analysis. This is a major drawback as some customers are interested in small RNA and in larger RNA such as mRNA and therefore, would need to perform an extra, separate isolation procedure in case also larger RNAs is of interest. Furthermore, a new sample or a new portion of an existing sample would need to be processed if after analysis of the small RNA an analysis of larger RNA is desired.

It is the object of the present invention to provide a nucleic acid isolation method, in particular an RNA isolation method, which overcomes at least one of the above disadvantages of the prior art methods. In particular, it was the object of the present invention to provide a method that allows to isolate small RNA as well as large RNA, which avoids the use of phenol and provides good RNA yields with different sample types, including protein rich samples.

SUMMARY OF THE INVENTION

The inventors have found that a nucleic acid isolation method which comprises a metal cation induced protein precipitation step prior to isolating a nucleic acid from the protein depleted supernatant can be significantly improved, if an organic solvent selected from aprotic polar solvents (e.g. DMSO or THF) and protic solvents (e.g. isopropanol or ethanol) is present in a concentration of 15% or less during the protein precipitation step. After removal of the precipitate, a protein-depleted supernatant is provided which comprises small (less than 200 nt) as well as large RNA (at least 1000 nt) and of course RNA of intermediate size if contained in the sample. All these RNA species can therefore be isolated from the protein-depleted supernatant, e.g. in form of total RNA or as one or more separate fractions enriched for the RNA of the desired size, respectively size range. Therefore, the method is particularly suitable for isolating RNA. Furthermore, as is shown in the examples, also DNA can be isolated from the obtained supernatant. Thereby, an improved nucleic acid isolation method is provided which gives the user flexibility with respect to the nucleic acid to be isolated.

According to a first aspect, a phenol-free method for isolating a nucleic acid from a sample is provided, said method comprising the following steps:
a) preparing a precipitation mixture by adding at least one metal cation precipitant and at least one organic solvent selected from aprotic polar solvents and protic solvents to the sample, wherein the precipitation mixture
   i) comprises the metal cation precipitant;
   ii) comprises the organic solvent in a concentration of 15% or less;
   iii) comprises at least one buffering agent; and
   iv) has an acidic pH value,
   and precipitating proteins;
b) separating the precipitate from the supernatant, wherein the supernatant comprises small RNA having a length of less than 200 nt and large RNA having a length of at least 1000 nt; and
c) isolating a nucleic acid from the supernatant.

The method is particularly suitable for isolating RNA as target nucleic acid from the sample. The examples show that the present invention provides a highly efficient method for isolating RNA from various sample types including samples from which it is particularly difficult to isolate RNA with good yield using a method that does not comprise a phenol-based extraction step. The present method provides comparable results even though no phenol or water-insoluble organic solvents such as chloroform are used for extracting proteins. The method provides after the metal cation induced precipitation step a protein-depleted supernatant which comprises small RNA, large RNA and in embodiments genomic DNA. One or more of the contained nucleic acid types can then be isolated from the supernatant. Therefore, the method allows e.g. the isolation of small as well as large RNA with good yield, thereby advantageously providing a method which provides more flexibility to the user. By providing a method which provides comparable RNA yields while avoiding the use of phenol, the present invention makes a major contribution to the art and also significantly improves existing phenol-free, precipitation based RNA isolation methods. Furthermore, the nucleic acid isolation method according to the present invention can be easily implemented into existing protocols which either aim at the isolation of small and/or large RNA or which aim at the parallel isolation of such RNA and also DNA from various samples, including protein rich samples such as blood, plasma or serum.

According to a second aspect, a phenol-free method for providing a protein depleted supernatant from a sample is provided, said method comprising the following steps:
a) preparing a precipitation mixture by adding at least one metal cation precipitant and at least one organic solvent selected from aprotic polar solvents and protic solvents to the sample, wherein the precipitation mixture
   i) comprises the metal cation precipitant;
   ii) comprises the organic solvent in a concentration of 15% or less;

iii) comprises at least one buffering agent; and
iv) has an acidic pH value,
and precipitating proteins; and
b) separating the precipitate from the supernatant, wherein the obtained supernatant comprises small RNA having a length of less than 200 nt and large RNA having a length of at least 1000 nt.

According to a third aspect, a precipitation buffer is provided which comprises
a) at least one metal cation precipitant;
b) at least one organic solvent selected from aprotic polar solvents and protic solvents;
c) at least one buffering agent; and
wherein the precipitation buffer has a pH value that lies in a range of 3 to 5.5.

Said precipitation buffer can be used e.g. for precipitating proteins from a disrupted biological sample, thereby providing after separation of the precipitate a protein-depleted supernatant which comprises small RNA having a length of less than 200 nt and large RNA having a length of at least 1000 nt and also RNA of intermediate size if contained in the sample. The contained RNA can then be isolated from the supernatant e.g. in form of total RNA or as one or more separate fractions enriched for RNA of a certain size, respectively size range (e.g. less than 200 nt or larger than 200 nt). Said precipitation buffer may be comprised in a kit for isolating nucleic acids such as in particular RNA.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

BRIEF DESCRIPTION OF THE FIGURES

In FIG. 9, the numbers have the following meaning: 1 (Marker); 2 (DMSO); 3 (acetone); 4 (THF); 5 (1,4 dioxane); 6 (DMF); 7 (acetonitrile); 8 (NMP); 9 (isopropanol); 10 (ethanol); 11 ($H_2O$); 12 (DMSO); 13 (Marker).

In FIG. 11, the numbers have the following meaning: 1 (Marker); 2 (citrate); 3 (MgOAc); 4 ($NH_4$OAc); 5 (KOAc); 6 (NaOAc); 7 ($H_2O$); 8 ($H_2O$+NaOAc); 9 (NaCl); 10 (NaOAc); 11 (XP (NaOAc)); 12 (XP (PIPPS)); 13 (Marker).

In FIG. 14, the numbers have the following meaning: 1 (Marker); 2 (0% DMSO); 3 (3.4% DMSO); 4 (6.9% DMSO); 5 (10.4% DMSO); 6 (13.7% DMSO); 7 (17.2% DMSO); 8 (25.6% DMSO); 9 (Marker); 10 (50 mM $ZnCl_2$); 11 (145 mM $ZnCl_2$); 12 (290 mM $ZnCl_2$); 13 (437 mM $ZnCl_2$); 14 (580 mM $ZnCl_2$); 15 (730 mM $ZnCl_2$).

DETAILED DESCRIPTION OF THE INVENTION

Figure 1:
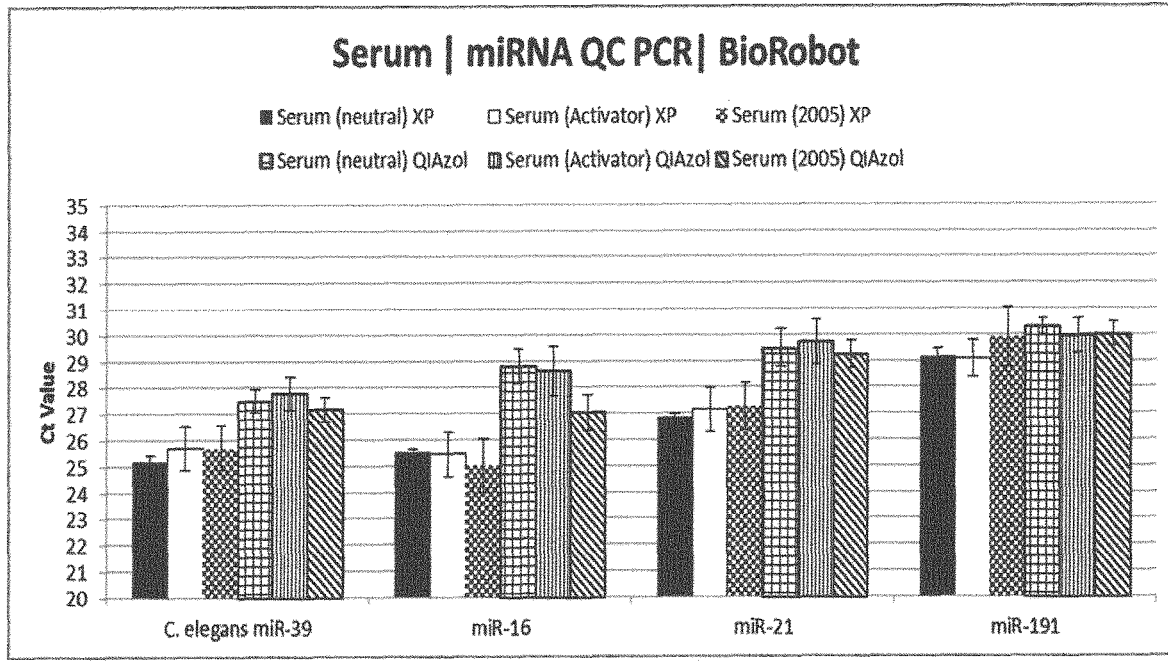
FIGS. 1 and 2: Shown are the quantitative RT-PCR results of the miScript miRNA QC PCR Array. The eluates obtained using different miRNA isolation protocols from serum and plasma with the BioRobot Universal using the two protocols "precipitation" (XP) and "miRNeasy" (QIAzol), the latter being a protocol which uses phenol during isolation, were analyzed. The mean values obtained from 8 replicates are shown including the standard deviation.

The present invention provides an improved protein precipitation based method for processing a RNA containing sample, which provides after precipitation a protein-depleted supernatant which comprises small as well as large RNA and in embodiments also DNA. One or more of the contained nucleic acid types can subsequently be isolated from the supernatant. The method is an improvement over prior art methods, because the protein-depleted supernatant comprises different kinds of RNA species, including small and large RNA and therefore, provides more flexibility to the user regarding the target nucleic acid to be isolated. Thus, one method is provided that can be used for the isolation of different nucleic acids.

A. Method for Isolating a Nucleic Acid from a Sample

According to a first aspect, a phenol-free method for isolating a nucleic acid from a sample is provided, said method comprising the following steps:
a) preparing a precipitation mixture by adding at least one metal cation precipitant and at least one organic solvent selected from aprotic polar solvents and protic solvents to the sample, wherein the precipitation mixture
   i) comprises the metal cation precipitant;
   ii) comprises the organic solvent in a concentration of 15% or less;
   iii) comprises at least one buffering agent; and
   iv) has an acidic pH value,
   and precipitating proteins;
b) separating the precipitate from the supernatant, wherein the supernatant comprises small RNA having a length of less than 200 nt and large RNA having a length of at least 1000 nt; and
c) isolating RNA from the supernatant.

Subsequently, we will explain each step and preferred embodiments thereof in detail.

Step a)—Protein Precipitation

In step a), a precipitation mixture containing the sample is prepared and proteins are precipitated. The sample is preferably a biological sample and may be e.g. a disrupted sample if sample disruption is necessary to release the nucleic acids. As is described subsequently, sample disruption may also occur during the protein precipitation step. To initiate precipitation, a (i.e. at least one) metal cation precipitant and an (i.e. at least one) organic solvent selected from aprotic polar solvents and protic solvents is added to the sample. Incorporating such organic solvent during the protein precipitation step in a concentration as described herein has the effect that the subsequently obtained protein-depleted supernatant comprises not only small RNA having a length of less than 200 nt (as is the case with prior art methods) but additionally comprises large RNA having a length of at least 1000 nt. Of course, the supernatant may also comprise RNA species of intermediate size if comprised in the sample. That not only small but also larger RNA species are comprised in the protein-depleted supernatant is advantageous, because the applicability of the method is broadened and the user may isolate different types of RNA. Furthermore, in embodiments, the supernatant also comprises DNA as is demonstrated in the examples.

The use of a metal cation precipitant for precipitating proteins is known in the prior art and suitable metal cation precipitants are also described (see e.g. Lovrien, R. E. and Matulis, 2001 "Selective precipitation of proteins. Current Protocols in Proteins Science. 7:4.5.1-4.5.36 or EP 2 163 622). Any metal cation capable of acting as a protein precipitant can be used in conjunction with the invention and examples include but are not limited to cations of Cd, Hg, Pb, Zn and Al. Also combinations of metal cation precipitants can be used. Preferably, the metal cation precipitant is selected from $Zn^{2+}$ or $Al^{3+}$. As is demonstrated by the examples, these metal cation precipitants have advantages, because $Zn^{2+}$ and $Al^{3+}$ initiate protein precipitation very rapidly and are also effective in low concentrations. The use of $Zn^{2+}$ is particularly preferred.

The metal cation precipitant is preferably added in form of a solution which comprises a dissolved salt of the metal cation precipitant. E.g. halogenide salts such as chloride salts may be used. The precipitation mixture that is provided in step a) may comprise the metal cation precipitant in a broad concentration range. As is shown by the examples, a concentration of approx. 50 mM zinc chloride in the precipitation mixture is already sufficient to precipitate proteins. Particularly preferred is a concentration in the precipitation mixture that is selected from 200 mM to 675 mM, 250 mM to 650 mM, 300 mM to 625 mM, 350 mM to 600 mM or 400 mM to 550 mM. As is demonstrated by the examples, these concentration ranges are particularly suitable to effect protein precipitation while providing a supernatant that comprises small as well as large RNA in high amounts. These concentration ranges are particularly useful if Zn is used as metal cation precipitant. According to one embodiment, the mentioned concentrations refer to the overall concentration of metal cation precipitants in the precipitation mixture if two or more metal cation precipitants are added to the precipitation mixture. According to one embodiment, a single metal cation precipitant, preferably $Zn^{2+}$ is used to prepare the precipitation mixture.

The precipitation mixture that is provided in step a) comprises an organic solvent selected from aprotic polar solvents and protic solvents in a concentration of 15% or less. The organic solvent used is a water-soluble organic solvent. If two or more respective organic solvents are included in the precipitation mixture, this concentration refers to the overall concentration of said organic solvents in the precipitation mixture. As is demonstrated by the examples, including such an organic solvent during the protein precipitation step in a concentration as defined herein has the technical effect that not only small RNA having a length of less than 200 nt is comprised in the protein depleted supernatant, but also large RNA having a length of at least 1000 nt. Of course, the supernatant also comprises RNA species of intermediate size if comprised in the sample. Therefore, also mRNA remains in the supernatant in large amounts and is in contrast to prior art methods (as are described e.g. in EP 2 163 622) not depleted along with the proteins and thus can be isolated subsequently from the obtained supernatant, if desired. Therefore, the present method allows to isolate RNA of different sizes, respectively size ranges from the protein-depleted supernatant which provides flexibility to the user of the method. However, as is demonstrated by the examples, it is important that the organic solvent as defined herein is comprised in the precipitation mixture in the right concentration. Already small amounts of the claimed organic solvents are effective to achieve the advantageous technical effects described herein and thus provide a supernatant which comprises small as well as large RNA. However, higher concentrations of the claimed organic solvent such as e.g. 17% or 25% in the precipitation mixture have a negative effect, because large RNA is under these conditions again depleted from the supernatant.

The precipitation mixture provided in step a) may comprise the organic solvent in a concentration selected from 2% to 15%, 3% to 15%, 5% to 14.5%, 6% to 14%, 7% to 13.5%, 8% to 13%, 9% to 12.5% or 9.5% to 12%. As is shown in the examples, these concentration ranges are suitable to provide a protein-depleted supernatant which comprises large amounts of small as well as large RNA. Of course, the supernatant also comprises RNA species of intermediate size if comprised in the sample. As described above, also two or more different organic solvents as claimed may be used in step a). In this case, the above indicated concentration ranges refer to the overall concentration of said organic solvents in the precipitation mixture. According to one embodiment, a single organic solvent as defined herein is used for preparing the precipitation mixture.

According to a preferred embodiment, the organic solvent is an aprotic polar solvent. Examples of such organic solvents include but are not limited to sulfoxides such as dimethylsulfoxide (DMSO), ketons such as acetone, nitriles such as acetonitrile, cyclic ethers such as tetrahydrofurane (THF) and 1,4 dioxane, lactames such as 1-methyl-2-pyrolidone (NMP) and tertiary carboxylic acid amides such as dimethyl-formamide (DMF). Such aprotic polar solvents are miscible in water. Thus, the aprotic polar solvent may be selected from sulfoxides, ketons, nitriles, cyclic ethers, lactames and tertiary carboxylic acid amides and preferably is selected from dimethylsulfoxide (DMSO), acetone, acetonitrile, tetrahydrofurane (THF), 1,4 dioxane, 1-methyl-2-pyrolidone (NMP) and dimethyl-formamide (DMF). As is demonstrated by the examples, these aprotic polar organic solvents are all suitable for the purpose of the present method and provide a protein-depleted supernatant which comprises small RNA, large RNA and additionally high molecular weight nucleic acids such as in particular genomic DNA. Therefore, using a polar aprotic organic solvent provides a protein-depleted supernatant which can be used for a broad range of downstream applications, because small RNA, large RNA, RNA species of intermediate size, as well as genomic DNA can be isolated therefrom if these types of nucleic acids are contained in the initial sample. This provides lots of flexibility to the user of the method. Particularly good results were achieved with DMSO, DMF, THF and NMP which therefore, are preferred aprotic polar organic solvents. Particularly preferred are DMSO and also NMP, which also have advantages regarding a reduced toxicity.

Furthermore, as is demonstrated by the examples, the organic solvent may also be a protic solvent. Polar protic solvents that can be used include linear or branched C1-C5 alcohols. Water-miscible alcohols such as isopropanol and ethanol are preferred and can be used as organic solvent. Also methanol is an alcohol miscible in water. These organic solvents also provide if used in the concentration ranges described herein a protein-depleted supernatant which comprises small RNA and large RNA in large amounts and of course also RNA of intermediate size if contained in the sample. As described above, also two or more of such organic solvents may be used wherein the overall concentration of these organic solvents in the precipitation mixture lies in the range/ranges described above.

The precipitation mixture that is provided in step a) has an acidic pH value. An acidic pH value has a beneficial effect as is shown in the examples. The pH value of the precipitation mixture may be $\leq 6$, $\leq 5.75$, $\leq 5.5$, $\leq 5.25$, preferably $\leq 5$, $\leq 4.75$, $\leq 4.5$ or $\leq 4.4$. Suitable ranges include 3 to 5.5, 3 to 5.25, 3.25 to 5, preferably 3.25 to 4.75, 3.5 to 4.5 or 3.75 to 4.4

To achieve and/or maintain the acidic pH value, the precipitation mixture comprises at least one buffering agent. As is demonstrated by the examples, different buffering agents are suitable and may be used. Also combinations of buffering agents may be used. According to one embodiment, the buffering agent is or is derived from a carboxylic acid. Carboxylic acids include mono-, di- or tri carboxylic acids. Preferably, the buffering agent is acetic acid or citric acid, respectively is an acetate or citrate. As is demonstrated by the examples, acetate and citrate can be added in form of different salts. E.g. an alkali metal salt such as a sodium or potassium salt may be used. According to one embodiment sodium acetate is used as buffering agent. Furthermore, also phosphate buffers such as PIPPS can be used. The buffering agent is used in a concentration that is capable of maintaining the pH value of the precipitation mixture in the range described above. According to one embodiment, the precipitation mixture comprises the buffering agent in a concentration that lies in a range selected from 60 mM to 400 mM, 75 mM to 375 mM, 100 mM to 350 mM, 125 mM to 300 mM and 150 mM to 275 mM. As is demonstrated by the examples, these concentration ranges are particularly suitable for carboxylic acids, respectively salts of carboxylic acids such as sodium acetate. A concentration that lies in the range of 125 mM to 300 mM or 150 mM to 275 mM achieves particularly good results.

According to a preferred embodiment, step a) comprises adding a precipitation buffer to the sample, wherein said precipitation buffer comprises at least one metal cation precipitant, at least one organic solvent as defined above and at least one buffering agent. Details with respect to the metal cation precipitant, the organic solvent and the buffering agent were described above. This embodiment is convenient, as the agents required to achieve protein precipitation and hence protein depletion while maintaining small as well as large RNA in the supernatant are contained in one buffer that is added to the sample. The sample is in one embodiment a disrupted sample.

The composition of the precipitation buffer is such that when adding the intended volume of precipitation buffer to a certain volume of the sample, which may be a disrupted sample, a precipitation mixture is provided that comprises the metal cation precipitant and the organic solvent in a concentration as described above. In certain embodiments, the sample, which may be a disrupted sample, is mixed with the precipitation buffer in a ratio in the range of from 1:1 to 1:20 (precipitation buffer:sample). In particular, the ratio may lie in the range of from 1:1.5 to 1:12, preferably 1:2 to 1:8, more preferably 1:2.5 to 1:5, most preferably 1:3 to 1:4 (precipitation buffer:sample). In specific embodiments, the precipitation buffer is added to the sample, which may be a disrupted sample, in a ratio of about 1:3.37 (precipitation buffer:sample).

The precipitation buffer that is added to the sample, which according to one embodiment is a disrupted sample, to establish the conditions of the precipitation mixture preferably comprises the metal cation precipitant in form of a dissolved salt. E.g. halogenide salts such as chloride salts can be used. The metal cation precipitant salt may be comprised in the precipitation buffer in a concentration selected from 0.75M to 3 M, 1M to 2.8M, 1.25M to 2.7M, 1.5M to 2.6M or 1.7M to 2.5M. As is demonstrated by the examples, using a precipitation buffer that comprises the metal cation precipitant in a respective concentration provides good results. Suitable metal cation precipitants were described above, preferably a metal cation precipitant selected from $Zn^{2+}$ and $Al^{3+}$ is used. Most preferred is $Zn^{2+}$ which can be added e.g. as zinc chloride.

The precipitation buffer may comprise the organic solvent in a concentration selected from 13% to 65%, 20% to 63%, 25% to 62.5%, 30% to 60%, 33% to 57.5%, 37.5% to 55% or 40% to 52.5%. Suitable examples for the organic solvent were described above and are also evident from the examples. The organic solvent is water-miscible. Preferably, the organic solvent is an aprotic polar solvent, such as DMSO. Of the protic organic solvents, water-miscible alcohols such as ethanol and isopropanol are preferred.

The precipitation buffer may have a pH value that is selected from 3 to 5.5, 3 to 5.25, 3.25 to 5, 3.25 to 4.75, 3.5 to 4.5 and 3.75 to 4.4. Particularly suitable is a pH of 3 to 5, 3.25 to 4.75, 3.5 to 4.5 or 3.75 to 4.4. The precipitation buffer is preferably suitable to establish and/or maintain a respective pH value in the precipitation mixture. As is demonstrated by the examples, using a precipitation buffer that has and maintains a respective acidic pH value provides advantageous results, in particular when processing protein rich samples such as plasma or serum. Suitable examples for buffering agents that can be used to maintain a respective pH value in the precipitation mixture were described above and are also evident from the examples. According to one embodiment, the precipitation buffer comprises the buffering agent in a concentration selected from 300 mM to 2M, 400 mM to 1.75M, 450 mM to 1.5M, 500 mM to 1.4M, 550 mM to 1.3M and 600 mM to 1.25M. Particularly preferred are carboxylic acid salts such as acetate or citrate salts, e.g. alkali metal salts which may be used in the before mentioned concentration ranges. Particularly preferred is a concentration that lies in the range of 550 mM to 1.3M, 600 mM to 1.25M or 650 mM to 1.2M.

When the precipitation mixture is provided, the proteins contained in the sample are precipitated. Precipitation can be assisted e.g. by agitation. Agitation includes but is not limited to vortexing, shaking, inverting and pipetting up and down. Furthermore, the sample may be cooled, e.g. stored on ice as is also described in the examples.

As described above, the precipitation mixture is prepared by adding the metal cation precipitant and the organic solvent as defined above to the nucleic acid containing sample. Non-limiting examples of suitable RNA containing biological samples are also described below. The present method is particularly suitable for isolating RNA from protein rich samples. Where necessary, the sample is disrupted. Therefore, according to one embodiment, the method encompasses a step of disrupting the sample. Thereby, nucleic acids such as in particular RNA are released and become accessible for the subsequent nucleic acid isolation step.

Different methods can be used in order to disrupt the sample. The term "disrupting" or "disruption" is used herein in broad sense and in particular encompasses the lysis of a sample. In a respective lysis step, biomolecules such as in particular RNA are released from cells or can be freed from other sample components such as e.g. proteins, thereby rendering the RNA accessible for isolation. Herein, it is referred to a respective disruption step also generally as lysis step, irrespective of whether biomolecules such as in particular nucleic acids are released from cells or whether the lysis is performed in order to release biomolecules such as nucleic acids e.g. from proteins or other substances comprised in the sample. Hence, the sample may comprise cells or may comprise no or only minor amounts of cells as is e.g. the case with blood plasma.

Different methods can be used in order to lyse the sample and suitable lysis methods are well-known in the prior art. Preferably, the sample is contacted for disruption, respectively lysis, with one or more lysing agents. These can be contained in a disruption reagent such as a lysis buffer. RNA should be protected during lysis from degradation by nucleases. The chosen lysis conditions may also vary depending on the type of sample to be processed. Generally, the lysis procedure may include but it is not limited to mechanical, chemical, physical and/or enzymatic actions on the sample. Examples include but are not limited to grinding the sample in a bead mill or in the presence of glass beads, homogenising the sample, the application of ultrasound, heating, the addition of one or more detergents and/or the addition of protein degrading compounds, such as for example protein degrading enzymes or salts. Furthermore, reducing agents such as beta-mercaptoethanol or DTT can be added for lysis to assist denaturation of e.g. nucleases. According to one embodiment, at least one chaotropic agent, such as preferably at least one chaotropic salt, is used for lysing and hence disrupting the sample. Suitable chaotropic agents and in particular suitable chaotropic salts are known to the skilled person and are also described herein. As is described herein, using a chaotropic salt for lysis has the advantage that it allows to introduce a chaotropic salt which may additionally support establishing suitable nucleic acid binding conditions in step c).

As is demonstrated by the examples, sample disruption may occur prior to addition of the metal cation precipitant and the organic solvent but may also occur at the same time respectively stage when the precipitation mixture is prepared. Depending on the sample to be processed, a lysis/binding composition may also be added after preparation of the precipitation mixture. This embodiment is less preferred though as it may reduce the RNA yield when processing complex samples such as blood or serum.

Thus, according to one embodiment, the sample is disrupted at the same time respectively stage when the metal cation precipitant and the organic solvent are added in step a). According to this embodiment, a phenol-free method for isolating a nucleic acid from a sample is provided, which comprises the following steps:
  a) preparing a precipitation mixture by adding at least one disruption reagent, at least one metal cation precipitant and at least one organic solvent selected from aprotic polar solvents and protic solvents to the sample to disrupt the sample and prepare a precipitation mixture which
    i) comprises the metal cation precipitant;
    ii) comprises the organic solvent in a concentration of 15% or less;
    iii) comprises at least one buffering agent; and
    iv) has an acidic pH value; and
    v) comprises the disruption reagent,
    and precipitating proteins;
  b) separating the precipitate from the supernatant, wherein the supernatant comprises small RNA having a length of less than 200 nt and large RNA having a length of at least 1000 nt; and
  c) isolating a nucleic acid from the supernatant.

Suitable disruption reagents such as lysis buffers that can be used are well known to the skilled person and are also described herein. Such disruption reagent may be added e.g. separately from the precipitation buffer or may be mixed with the precipitation buffer in advance so that then a mixture of the precipitation buffer and the disruption reagent is added to the sample in step a). According to one embodiment, the disruption reagent comprises a chaotropic salt. Suitable examples are known and also described herein.

According to a preferred embodiment, the sample is disrupted prior to adding the metal cation precipitant and the organic solvent in step a). According to this embodiment, a phenol-free method for isolating a nucleic acid from a sample is provided, which comprises the following steps:
  x) disrupting the sample;
  a) preparing a precipitation mixture by adding at least one metal cation precipitant and at least one organic solvent selected from aprotic polar solvents and protic solvents to the disrupted sample to prepare a precipitation mixture which
    i) comprises the metal cation precipitant;
    ii) comprises the organic solvent in a concentration of 15% or less;
    iii) comprises at least one buffering agent; and
    iv) has an acidic pH value,
    and precipitating proteins;
  b) separating the precipitate from the supernatant, wherein the supernatant comprises small RNA having a length of less than 200 nt and large RNA having a length of at least 1000 nt; and
  c) isolating a nucleic acid from the supernatant.

According to one embodiment, for disrupting the sample, a disruption composition is provided which comprises the sample to be disrupted and in addition thereto a chaotropic agent, preferably a chaotropic salt, in a concentration selected from the group consisting of 0.5 M to saturation, 0.75M to 5M, 1 M to 4.5M and 1.25M to 4.25M. Chaotropic salts include but are not limited to guanidinium salts such as guanidinium hydrochloride, guanidinium thiocyanate (or guanidinium isothiocyanate (GITC)) or chaotropic salts comprising thiocyanate, iodide, perchlorate, trichloroacetate or trifluroacetate and the like. Such chaotropic salts can be provided e.g. as sodium or potassium salts. Preferably, the chaotropic salt is GTC (GITC) or an equally strong chaotropic salt. Respective strong chaotropic salts are advantageous as they may also efficiently protect the RNA comprised in the composition from enzymatic degradation. Also urea may be used to support the disruption of the sample. According to one embodiment, the disruption composition is provided in step x) and hence prior to adding the metal cation precipitant and the organic solvent in step a) to said disruption composition.

Furthermore, during lysis, also other additives can be added such as chelating agents, nuclease inhibitors, in particular RNase inhibitors or DNase inhibitors (if the parallel isolation of RNA and DNA is intended) and the like. Respective additives that can be used to support the lysis of a sample and to protect the released nucleic acids, in particular the released RNA, are well-known in the prior art and thus, do not need to be described in detail herein.

The disrupted sample obtained from the sample in step x) may also optionally be further processed prior to preparing the precipitation mixture in step a). For example, the lysate can be homogenized; homogenization may also occur during the disruption/lysis process itself. Furthermore, the lysate can be cleared in order to remove cell debris. Lysate clearing methods may involve filtration and/or binding the cell debris and other contaminants to appropriate surfaces, such as for example surfaces carrying ionic groups, in particular anionic groups such as carboxyl groups.

The method of the present invention may be combined with a proteolytic digest. Even if a proteolytic digest is performed, the precipitation based method of the invention can still improve the results by depleting residual proteins. The term "protein" as used herein also encompasses peptides. However, it is an advantage of the present invention that it does not require a time consuming proteolytic enzymatic digestion step. Therefore, according to one embodiment, disruption of the sample does not involve the use of a proteolytic enzyme. A proteolytic enzyme refers to an enzyme that catalyzes the cleavage of peptide bounds, for example in proteins, polypeptides, oligopeptides and peptides. Exemplary proteolytic enzymes include but are not limited to proteinases and proteases in particular subtilisins, subtilases, alkaline serine proteases and the like. Subtilases are a family of serine proteases, i.e. enzymes with a serine residue in the active side. Subtilisins are bacterial serine protease that has broad substrate specificities. Subtilisins are relatively resistant to denaturation by chaotropic agents, such as urea and guanidine hydrochloride and anionic detergents such as sodium dodecyl sulfate (SDS). Exemplary subtilisins include but are not limited to proteinase K, proteinase R, proteinase T, subtilisin, subtilisin A, QIAGEN Protease and the like.

Step b)—Removal of the Precipitate

In step b) the formed precipitate is separated from the remaining sample, herein referred to as "supernatant". Separation can be assisted by various means such as e.g. sedimentation, centrifugation or filtration. The term "supernatant" is used herein in particular to describe the precipitation mixture from which the formed precipitate was removed. The term "supernatant" is therefore not limited to a specific precipitate depleted precipitation mixture that was obtained by a certain mode of precipitate separation. Thus, the term "supernatant" e.g. encompasses embodiments wherein the precipitate is collected at the bottom of a vessel and wherein the remaining sample is removed as supernatant as well as embodiments wherein the precipitation mixture is passed through a filter to remove the formed precipitate and recover the remaining sample in form of a flow-through.

As is demonstrated by the examples, due to the precipitation conditions used in the method according to the invention, the obtained supernatant comprises small RNA having a length of less than 200 nt and in addition thereto large RNA having a length of at least 1000 nt. Of course, also RNA of intermediate size is comprised in said supernatant if comprised in the original sample. According to one embodiment, the obtained supernatant comprises at least 60%, at least 65%, at least 70%, at least 75% or at least 80% of the RNA molecules having a length of at least 1000 nt that are contained in the original sample. It was also found that the large RNA recovery rates are as high. Thus, in contrast to prior art precipitation based methods, the present method allows the recovery and isolation of large RNA molecules with good yield. Additionally, high molecular weight nucleic acids such as genomic DNA can be comprised in said supernatant depending on the used precipitation conditions.

Step c)—Isolating a nucleic acid from the supernatant

In step c), a nucleic acid is isolated from the obtained supernatant. The nucleic acid may be RNA, DNA or both. For isolating the one or more target nucleic acids (e.g. RNA and/or DNA) of interest from the obtained supernatant, methods known in the prior art may be used. Examples of suitable isolation methods include but are not limited to silica-based purification methods, magnetic particle-based purification methods, chromatography based purification procedures, anion-exchange chromatography (using anion-exchange surfaces, such as columns or magnetic particles), precipitation and combinations thereof. Preferably, one or more of the target nucleic acids such as RNA and/or DNA is isolated from the supernatant by binding the nucleic acid to a solid phase using appropriate binding conditions. The solid phase may e.g. provide a silica binding surface or may carry anion exchange functional groups which can bind the nucleic acid of interest. With respect to the latter embodiment, e.g. isolation methods that are based on the charge-switch principle may be used.

Preferably, at least RNA is isolated from the supernatant. For isolating RNA from the obtained supernatant, methods known in the prior art can be used. The method according to the invention has the advantage that the supernatant comprises small as well as large RNA. Therefore, the user may, depending on the target RNA of interest, isolate either small RNA, large RNA or both from the supernatant. Small and large RNA may be isolated in separate fractions or may be isolated in form of total RNA or total nucleic acids from the supernatant. Of course, also RNA of intermediate size is comprised in the supernatant if comprised in the sample and can be isolated e.g. together with the large RNA and/or the small RNA.

Preferably, RNA is isolated by binding it to a nucleic acid binding solid phase in the presence of an organic solvent such as an alcohol. Binding to the solid phase can be enhanced in the presence of a chaotropic salt in the binding mixture. Non-limiting embodiments are described subsequently.

According to one embodiment, total RNA is isolated from the supernatant, wherein said total RNA includes small as well as large RNA and RNA of intermediate size. In this embodiment, step c) preferably comprises:

aa) adding at least one alcohol to the supernatant to provide a binding mixture which comprises the alcohol in a concentration ≥35%, preferably ≥40%, more preferred ≥45%;

bb) binding total RNA contained in the binding mixture to a nucleic acid binding solid phase, wherein after step bb), large and small RNA is bound to the solid phase;

cc) optionally washing the bound RNA; and dd) eluting RNA from the solid phase.

It is a well-established principle that large RNA as well as small RNA and of course RNA of intermediate size can bind to a nucleic acid binding solid phase in the presence of a high concentration of alcohol. Therefore, the present method allows in this embodiment to isolate total RNA which comprises small RNA, large RNA and RNA of intermediate size. Respective methods are also described in the background of the invention.

Using an alcohol concentration of at least 35%, preferably at least 40%, more preferred at least 45% or at least 50% in the binding mixture during the binding step has the effect that RNA binding conditions are established that allow to bind small RNA to the nucleic acid binding solid phase. Here, it was surprisingly found that also lower alcohol concentrations can be used in conjunction with the present method than are commonly used in the prior art to achieve binding of small RNA to the solid phase. Without wishing to be bound in theory, it is believed that this is because the organic solvent used in the precipitation mixture contributes to establishing suitable binding conditions. Of course, also longer RNA molecules can bind under these conditions and thus are captured in the total RNA.

The alcohol may be a branched or unbranched aliphatic alcohol with 1 to 5 carbon atoms and may be selected from methanol, ethanol, propanol, isopropanol and butanol and mixtures thereof. Also mixtures of alcohol can be used. Preferably, isopropanol and/or ethanol is used as alcohol to establish the binding conditions. These alcohols are commonly used to isolate small and large RNA from disrupted samples. Particularly preferred is isopropanol. Due to the protein precipitation step that is performed in advance, a high alcohol concentration can be used in the binding mixture because the risk is reduced that proteins precipitate during the binding step and e.g. clog the nucleic acid binding solid phase or otherwise interfere with RNA binding. This is beneficial with respect to the yield. The alcohol concentration in the binding mixture may be ≥50% (v/v), ≥55% (v/v) or ≥60% (v/v). Suitable ranges for the alcohol concentration in the binding mixture include but are not limited to ≥40% (v/v) to ≤80% (v/v), ≥45% (v/v) to ≤75% (v/v), ≥50% (v/v) to ≤70% (v/v) and ≥55% (v/v) to ≤65% (v/v). Respective alcohol concentrations can be used in step aa). As discussed, ethanol and isopropanol are preferred.

According to one embodiment, binding of the RNA to a nucleic acid binding solid phase is enhanced by incorporating a chaotropic salt in the binding mixture. Suitable concentrations for chaotropic salts are known to the skilled person and are described herein.

According to one embodiment, the binding mixture of step aa) comprises a chaotropic salt in a concentration which lies in a range of 0.1M up to the saturation limit. The concentration may be selected from 0.2M to 5M, 0.25M to 4.5M, 0.3M to 4.25M, 0.35 to 4M and 0.4M to 3.75M. Higher concentrations of chaotropic salts can be favourable to increase the yield of RNA. Chaotropic salts include but are not limited to guanidinium salts such as guanidinium hydrochloride, guanidinium thiocyanate (or guanidinium isothiocyanate (GITC)) or chaotropic salts comprising thiocyanate, iodide, perchlorate, trichloroacetate or trifluroacetate and the like. Also mixtures of chaotropic salts may be used. Such chaotropic salts can be provided e.g. as sodium or potassium salts. Preferably, the chaotropic salt is GTC or GITC or an equally strong chaotropic salt. The chaotropic salt present in the binding mixture may have been introduced during lysis, as the use of chaotropic agents, in particular chaotropic salts, for lysis is preferred for disrupting the sample. Details were described above. This procedure was also used in the examples. A chaotropic salt may also be added during step c) either to introduce a chaotropic salt into the binding mixture or to increase the concentration of the chaotropic salt during the RNA binding step. Thus, it is also within the scope of the present invention to increase the concentration of chaotropic salt for binding, by adding a further amount of chaotropic salt in the RNA isolation step c). Furthermore, additional additives can be added to improve RNA binding, such as e.g. detergents.

In step bb), small and large RNA and RNA of intermediate size contained in the binding mixture resulting from step aa) are bound to a nucleic acid binding solid phase. Solid phases suitable for RNA binding are known to the skilled person; exemplary suitable nucleic acid binding solid phases are also described below. According to one embodiment, the binding mixture resulting from step aa) is contacted with a solid phase in step bb). This embodiment is particularly suitable if a nucleic acid binding phase comprised in a column is used. If a column based procedure is used, a nucleic acid binding solid phase may be used in step bb) in order to bind total RNA, including small RNA, to the solid phase. In case particles are used, they may also be present already in step aa) or may be introduced in step bb).

After RNA including small RNA was bound in step bb) to the nucleic acid binding solid phase, the bound RNA may optionally be washed in step cc). For this purpose common washing solutions may be used. According to one embodiment, the solution used for washing comprises at least one chaotropic agent and/or at least one alcohol. Chaotropic agents that can be used in the washing solutions include but are not limited to chaotropic salts such as guanidinium hydrochloride, guanidinium thiocyanate, guanidinium isothiocyanate and sodium iodide. Other chaotropic salts are also described above. As alcohol, short chained branched or unbranched alcohols with preferably 1 to 5 carbon atoms can be used for washing, respectively in the washing solution. Examples are methanol, ethanol, propanol, isopropanol and butanol. Preferably, isopropanol and/or ethanol are used. However, also washing solutions without a chaotropic agent can be used.

An example of a suitable washing solution which can be used either alternatively or also in addition to the washing solutions described above comprises an alcohol and a buffer. Suitable alcohols are described above. Preferably, isopropanol or ethanol, most preferred ethanol is used for this washing step. Preferably, ethanol is used in a concentration of at least 60% (v/v), at least 70% (v/v), preferably at least 80% (v/v). According to one embodiment, the solution used for washing comprises at least one chaotropic agent, at least one alcohol, at least one detergent and/or at least one buffering agent. Suitable buffering agents such as Tris or citrate can be used; suitable buffering agents are also known to the skilled person.

Either prior to or subsequent to the optional one or more washing steps described above, a DNase digest may be performed. Such DNase digest may be performed e.g. while the RNA is bound to the nucleic acid binding solid phase. Thereby, the amount of genomic DNA contaminations in the isolated RNA can be reduced if only RNA is the nucleic acid of interest. Suitable embodiments for performing a respective DNase digest are described herein and are also known in the prior art. A respective DNase digestion step is optional. The conditions used for performing the DNase digest while the RNA is bound to the nucleic acid binding solid phase can result in that RNA and in particular small RNA is partially released from the nucleic acid binding solid phase. Therefore, it is preferred to ensure that potentially released small RNA is re-bound to the nucleic acid binding solid phase to ensure a high recovery of small RNA. Depending on the type of nucleic acid binding solid phase used, e.g. whether a column based or particle based approach is used, different procedures are feasible. If particles such as magnetic particles are used as nucleic acid binding solid phase, after performing the optional DNase digest, a chaotropic agent and alcohol can be added, thereby establishing binding conditions that allow to rebind small RNA to the particles. For this purpose, a solution can be used which comprises e.g. a chaotropic salt and/or alcohol. A respective solution may also serve as washing solution. Additional alcohol can also be added separately, in order to increase the alcohol concentration for re-binding. Suitable alcohols, alcohol concentrations, chaotropic salts and chaotropic concentrations were described above in conjunction with step c). The same conditions can be used for rebinding. If a column based nucleic acid binding solid phase is used it is preferred to perform the following steps after performing the optional DNase digest while the RNA is bound to the solid phase (often also referred to as on-column DNase digest):

collecting small RNA which might have been released from the nucleic acid binding solid phase during the DNAase digest as flow through;
contacting said flow through which comprises small RNA mixed with a recovery solution with the nucleic acid binding solid phase for rebinding the contained small RNA to said nucleic acid binding solid phase.

To ensure that RNA that might have been partially released during the on-column DNase digest rebinds to the nucleic acid binding solid phase and to collect released small RNA as flow through, it is preferred to pass a recovery solution through the column after the DNase digest was completed. RNA that can rebind under the conditions that are established by the recovery solution is tightly rebound to the nucleic acid binding solid phase and "escaped" small RNA can be collected as flow through and thus can be reapplied and accordingly can be rebound to the nucleic acid solid phase. This prevents that small RNA gets lost even if an on-column DNase digest is performed. Details of a respective rebinding step following an on column DNase digest are described in WO 2012/028737, herein incorporated by reference. After rebinding potentially escaped small RNA to the nucleic acid binding solid phase, again one or more washing steps can be performed. Suitable conditions were described above.

In case it is desired to perform an elution step to elute the RNA from the solid phase, elution can be achieved for example with classical elution solutions such as water, elution buffers, in particular low salt elution buffers. The elution buffers may comprise a biological buffer such as Tris, MOPS, HEPES, MES, BIS-TRIS propane and others. A respective elution step may be performed in step dd). Preferably, elution solutions are used that do not interfere with the intended downstream applications. After elution, the eluate can be heat denatured. However, it is also within the scope of the present invention to release and thus elute the nucleic acids from the solid phase by other or assisting elution means such as e.g. heating.

Subsequently, suitable embodiments are described which allow to isolate total RNA including small RNA from a sample comprising RNA and DNA. Here, embodiments are described which allow to isolate total RNA, including small RNA or which allow to isolate small RNA as separate fraction from larger RNA and/or in parallel with DNA. Thus, RNA as well as DNA can be isolated from the protein-depleted supernatant that is provided according to the method of the present invention. However, if desired, DNA can be selectively depleted during the purification process thereby providing isolated RNA which is substantially free of DNA, in particular free of genomic DNA. Here, different options exist to remove the DNA. Non-limiting embodiments will be described subsequently.

According to one embodiment, the supernatant obtained in step b) comprises RNA as well as DNA, and RNA and DNA are isolated in step c) by binding both types of nucleic acids to a nucleic acid binding solid phase. RNA and DNA may be eluted in form of total nucleic acids. According to one embodiment, which is feasible if RNA and DNA are both bound to the nucleic acid binding solid phase, a differential elution process can be followed thereby allowing to separately isolate DNA from total RNA, which includes large and small RNA. E.g. the DNA can be selectively eluted prior to eluting the bound RNA or vice versa. Respective differential elution conditions are e.g. described in WO 95/21849 or EP 1 693 453.

According to one embodiment, DNA is removed by selectively binding DNA under appropriate conditions to a nucleic acid solid phase and then separating the DNA bound to the nucleic acid binding solid phase from the remaining supernatant which still comprises the small and large RNA. This can be achieved e.g. by contacting the supernatant with a suitable nucleic acid binding solid phase under conditions wherein mainly DNA but not RNA is bound to the solid phase. Suitable nucleic acid binding solid phases which allow binding of DNA are well-known in the prior art and are also desired therein. In general, the nucleic acid binding solid phases described herein for the RNA binding step, in particular the silicon containing solid phases, can also be used for DNA binding. Suitable methods for selectively binding and thus removing DNA are for example described in EP 0 880 537 and WO 95/21849, herein incorporated by reference. E.g. if lysing the sample using chaotropic agents such as chaotropic salts, binding conditions can be established in the absence of short chained alcohols such as ethanol or isopropanol that are selective for DNA. If desired, the bound DNA may be further used, e.g. further processed and can e.g. optionally be washed and eluted from the nucleic acid binding solid phase thereby providing a DNA fraction which is substantially free of RNA. The respective DNA fraction is then available for analysis. Thus, the present invention also provides a method wherein RNA and DNA may be isolated from the same sample, because in contrast to prior art methods, a protein-depleted supernatant can be provided which comprises besides small and large RNA also DNA, such as genomic DNA. However, if DNA is not of interest, the bound DNA may also be simply discarded if intending to isolate (only) RNA, e.g. small and large RNA either in separate fractions or in form of total RNA, what is preferred. Also in this case such a DNA binding and removal step is favourable, as it reduces the amount of DNA contaminations in the purified RNA.

When binding DNA to a nucleic acid binding solid phase, such as e.g. a silica containing solid phase, and separating the bound DNA from the remaining sample, a DNA depleted RNA containing supernatant is provided from which small RNA as well as large RNA and RNA of intermediate size can be isolated.

In order to further reduce the amount of DNA in the isolated RNA, an intermediate step for degrading DNA using a suitable enzyme can be performed after DNA was removed from the protein-depleted supernatant by binding the DNA to a nucleic acid solid phase as described above. Performing a DNase digest allow to remove remaining traces of DNA. A DNase treatment may be performed after the RNA was bound to the nucleic acid binding solid phase, e.g. as on column DNase digest. Details were described above. Furthermore, a DNase digest may also be performed on the obtained RNA containing eluate.

Furthermore, it is within the scope of the present invention to isolate large RNA and small RNA in form of separate fractions. This can be achieved e.g. by binding RNA having a length >200 nt in a first step to a first nucleic acid binding solid phase using conditions that are selective for such larger RNA species. Thereby, the predominant portion of such larger RNA is bound to the solid phase, while the remaining supernatant comprises small RNA. In a second binding step, small RNA having a length of 200 nt or less is then isolated from the remaining supernatant from which the large RNA was removed. Respective selective binding conditions are well known in the prior art and therefore, do not need to be described in detail. They are also described in the background. Usually, for selectively binding large RNA in the first binding step, an alcohol concentration of less than 40% is used in the binding mixture, e.g. in a concentration that lies in the range of 10% to 37%, 15% to 35% or 20% to 30%, preferably in the presence of a chaotropic salt. After separating the large RNA that was bound to the solid phase, the supernatant remainder still comprises small RNA. The small RNA may then be isolated in a second binding step, e.g. by increasing the alcohol concentration to ≥40%, preferably ≥45%, more preferably ≥50% and binding the small RNA to a nucleic acid binding solid phase. The bound RNA may be washed and eluted. Furthermore, total RNA may be bound to the same solid phase and small RNA can be obtained as enriched fraction separate from larger RNA following e.g. a differential elution protocol. However, it is preferred to isolate total RNA which comprises small RNA having a length of less than 200 nt as well as larger RNA species because such a procedure is very convenient for the user and flexible with respect to the downstream applications of the isolated RNA, because RNA of all sizes (small, intermediate and large) are recovered.

Also other RNA isolation methods can be used in order to isolate RNA from the protein depleted supernatant that is provided using the special precipitation conditions of the invention. RNA isolation methods are e.g. also described in EP 2 163 622 and WO 2009/070558 and the described binding conditions can be used in order to isolate RNA from the supernatant. Generally, under conditions that are suitable to bind small RNA to a nucleic acid binding solid phase, larger RNA will also bind.

Furthermore, DNA may be isolated from the supernatant. Suitable methods are known to the skilled person and also evident from the present disclosure. According to one embodiment, total nucleic acids are isolated from the supernatant. Here, the isolated nucleic acids comprise small RNA, large RNA, RNA of intermediate size as well as DNA. Suitable binding conditions are known to the skilled person and are also evident from the present disclosure.

The isolated nucleic acids can then be analyzed and/or further processed using suitable assay and/or analytical methods. E.g. RNA such as small, large and/or RNA of intermediate size as well as DNA if isolated from the supernatant can be identified, modified, contacted with at least one enzyme, amplified, reverse transcribed, sequenced, contacted with a probe, be detected (their presence or absence) and/or can be quantified. Respective methods are well-known in the prior art and are commonly applied in the medical, diagnostic and/or prognostic field in order to analyze RNA. Thus, the recovered nucleic acids can be analyzed e.g. to identify the presence, absence or severity of a disease state including but not being limited to a multitude of neoplastic diseases, in particular premalignancies and malignancies such as different forms of tumors or cancers. E.g. the isolated nucleic acids can be analyzed in order to detect diagnostic and/or prognostic markers (e.g., fetal- or tumor-derived extracellular nucleic acids) in many fields of application, including but not limited to non-invasive prenatal genetic testing respectively screening, disease screening, pathogen screening, oncology, cancer screening, early stage cancer screening, cancer therapy monitoring, genetic testing (genotyping), infectious disease testing, injury diagnostics, trauma diagnostics, transplantation medicine or many other diseases and, hence, are of diagnostic and/or prognostic relevance. Thus, as discussed above, the present method may comprise a further step of nucleic acid analysis and/or processing.

Therefore, according to one embodiment, the isolated nucleic acids, such as in particular the isolated RNA, are analyzed to identify, detect, screen for, monitor or exclude a disease and/or at least one fetal characteristic. The analytical methods will depend on the nucleic acid species of interest. The analysis/further processing of the isolated nucleic acids can be performed using any nucleic acid analysis/processing method including, but not limited to amplification technologies, polymerase chain reaction (PCR), isothermal amplification, reverse transcription polymerase chain reaction (RT-PCR), quantitative real time polymerase chain reaction (Q-PCR), digital PCR, gel electrophoresis, capillary electrophoresis, mass spectrometry, fluorescence detection, ultraviolet spectrometry, hybridization assays, RNA or DNA sequencing, next generation sequencing, restriction analysis, reverse transcription, NASBA, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof.

In particular, the present method can be used for the isolation of RNA for any purpose for which the isolation of RNA is commonly desired. Non-limiting examples include, but are not limited to the isolation of RNA for subsequent cDNA synthesis, cDNA library construction, amplification based methods such as reverse transcription PCR, subtractive hybridization, in vitro translation, SAGE technology, expression analysis, expression array and expression-chip analysis, microarray analysis, RNAse and Si nuclease protection, RNA northern, dot, and slot blotting, micro injection and furthermore, for sequencing applications. Respective technologies are well-known to the skilled person and thus, do not need further description here. The method of the invention is efficient, flexible and does not require the use of phenolic compounds.

SPECIFIC EMBODIMENTS

Non-limiting specific embodiments of the method of the invention will be described in the following.

According to one embodiment, the method comprises the following steps
a) preparing a precipitation mixture by adding at least one metal cation precipitant in form of a dissolved salt and at least one organic solvent which is selected from aprotic polar solvents and protic solvents to the sample, wherein in case a protic solvent is used preferably the protic solvent is a water-miscible alcohol, more preferred selected from ethanol and isopropanol, and wherein the precipitation mixture
   i) comprises the metal cation precipitant salt in a concentration selected from 300 mM to 625 mM, 350 mM to 600 mM or 400 mM to 550 mM;
   ii) comprises the organic solvent in a concentration selected from 6.5% to 14.5%, 7% to 14%, 8% to 13.5%, 9% to 13% or 9.5% to 12%;
   iii) comprises at least one buffering agent; and
   iv) has an acidic pH value that lies in the range of 3 to 5.25, 3.25 to 5.0, 3.25 to 4.75, 3.5 to 4.5 or 3.75 to 4.4;
   and precipitating proteins;
b) separating the precipitate from the supernatant, wherein the supernatant comprises small RNA having a length of less than 200 nt and large RNA having a length of at least 1000 nt; and
c) isolating at least small and large RNA from the supernatant, wherein step c) comprises:
   aa) adding at least one alcohol to the supernatant to provide a binding mixture which comprises the alcohol in a concentration ≥40%, ≥45% or ≥50%;
   bb) binding total RNA contained in the binding mixture to a silicon containing nucleic acid binding solid phase, wherein after step bb), at least large and small RNA is bound to the solid phase;
   cc) optionally washing the bound RNA; and
   dd) eluting RNA from the solid phase.

As described above, according to one embodiment, prior to step a), a step x) is performed in which the sample is disrupted. However, as is described and also evident from the examples, sample disruption (if necessary) may also occur at the same time as the preparation of the precipitation mixture. Preferably, a precipitation buffer is added in step a) which comprises a metal cation precipitant in form of a dissolved salt, an organic solvent as defined herein and a buffering agent in suitable concentrations and with a suitable pH to provide the defined precipitation mixture.

According to one embodiment, the method is for isolating RNA and comprises the following steps
x) disrupting the sample;
a) preparing a precipitation mixture by adding at least one metal cation precipitant and at least one organic solvent selected from aprotic polar solvents and protic solvents to the disrupted sample, wherein in case a protic solvent is used the protic solvent preferably is a water-miscible alcohol, and wherein the precipitation mixture
   i) comprises the metal cation precipitant in a concentration selected from 300 mM to 625 mM, 350 mM to 600 mM or 400 mM to 550 mM;

ii) comprises the organic solvent in a concentration selected from 6.5% to 14.5%, 7% to 14%, 8% to 13.5%, 9% to 13% or 9.5% to 12%;
iii) comprises at least one buffering agent; and
iv) has an acidic pH value that lies in the range of 3 to 5.25, 3 to 5, 3.25 to 4.75, 3.5 to 4.5 or 3.75 to 4.4, and precipitating proteins;
b) separating the precipitate from the supernatant, wherein the supernatant comprises small RNA having a length of less than 200 nt and large RNA having a length of at least 1000 nt; and
c) isolating at least small and large RNA from the supernatant, wherein step c) comprises:
aa) adding at least one alcohol to the supernatant to provide a binding mixture which comprises the alcohol in a concentration ≥40%, ≥45% or ≥50%;
bb) binding total RNA contained in the binding mixture to a silicon containing nucleic acid binding solid phase, wherein after step bb), at least large and small RNA is bound to the solid phase;
cc) optionally washing the bound RNA;
dd) eluting RNA from the solid phase.

According to one embodiment, the method comprises the following steps
x) disrupting the sample;
a) preparing a precipitation mixture by adding at least one metal cation precipitant selected from $Zn^{2+}$ and $Al^{3+}$ in form of a dissolved salt, preferably zinc chloride, and at least one organic solvent which is an aprotic polar solvent to the disrupted sample, wherein the precipitation mixture
i) comprises the metal cation precipitant salt in a concentration selected from 300 mM to 625 mM, 350 mM to 600 mM or 400 mM to 550 mM;
ii) comprises the organic solvent in a concentration selected from 8% to 13.5%, 9% to 13% or 9.5% to 12%;
iii) comprises at least one buffering agent; and
iv) has an acidic pH value that lies in the range of 3.5 to 4.5 or 3.75 to 4.4;
and precipitating proteins;
b) separating the precipitate from the supernatant, wherein the supernatant comprises small RNA having a length of less than 200 nt and large RNA having a length of at least 1000 nt; and c) isolating small and large RNA from the supernatant, wherein step c) comprises:
aa) adding at least one alcohol to the supernatant to provide a binding mixture which comprises the alcohol in a concentration ≥40%, ≥45% or ≥50% and wherein the binding mixture additionally comprises a chaotropic salt;
bb) binding total RNA contained in the binding mixture to a silicon+containing nucleic acid binding solid phase, wherein after step bb), at least large and small RNA is bound to the solid phase;
cc) washing the bound RNA; and
dd) eluting RNA from the solid phase.

As described above, preferably, a precipitation buffer is added in step a) which comprises the metal cation precipitant in form of a dissolved salt, the organic solvent and the buffering agent in suitable concentrations and with a suitable pH to provide the defined precipitation mixture.

As described, according to one embodiment, the sample is disrupted at the same time respectively stage when the metal cation precipitant and the organic solvent are added in step a). According to one embodiment, the method is for isolating RNA, wherein the method comprises the following steps
a) preparing a precipitation mixture by adding at least one disruption reagent, at least one metal cation precipitant and at least one organic solvent selected from aprotic polar solvents and protic solvents to the sample, wherein in case a protic solvent is used the protic solvent preferably is a water-miscible alcohol, to disrupt the sample and prepare a precipitation mixture which
i) comprises the metal cation precipitant in a concentration selected from 300 mM to 625 mM, 350 mM to 600 mM or 400 mM to 550 mM;
ii) comprises the organic solvent in a concentration selected from 6.5% to 14.5%, 7% to 14%, 8% to 13.5%, 9% to 13% or 9.5% to 12%;
iii) comprises at least one buffering agent;
iv) has an acidic pH value that lies in the range of 3 to 5.25, 3 to 5, 3.25 to 4.75, 3.5 to 4.5 or 3.75 to 4.4; and
v) comprises the disruption reagent,
and precipitating proteins;
b) separating the precipitate from the supernatant, wherein the supernatant comprises small RNA having a length of less than 200 nt and large RNA having a length of at least 1000 nt; and
c) isolating at least small and large RNA from the supernatant, wherein step c) comprises:
aa) adding at least one alcohol to the supernatant to provide a binding mixture which comprises the alcohol in a concentration ≥40%, ≥45% or ≥50%;
bb) binding total RNA contained in the binding mixture to a silicon containing nucleic acid binding solid phase, wherein after step bb), at least large and small RNA is bound to the solid phase;
cc) optionally washing the bound RNA;
dd) eluting RNA from the solid phase.

According to one embodiment, said method comprises the following steps
a) preparing a precipitation mixture by adding at least one disruption reagent, at least one metal cation precipitant selected from $Zn^{2+}$ and $Al^{3+}$ in form of a dissolved salt, preferably zinc chloride, and at least one organic solvent which is an aprotic polar solvent to disrupt the sample and prepare a precipitation mixture which
i) comprises the metal cation precipitant salt in a concentration selected from 300 mM to 625 mM, 350 mM to 600 mM or 400 mM to 550 mM;
ii) comprises the organic solvent in a concentration selected from 8% to 13.5%, 9% to 13% or 9.5% to 12%;
iii) comprises at least one buffering agent;
iv) has an acidic pH value that lies in the range of 3.5 to 4.5 or 3.75 to 4.4; and
v) comprises the disruption reagent,
and precipitating proteins;
b) separating the precipitate from the supernatant, wherein the supernatant comprises small RNA having a length of less than 200 nt and large RNA having a length of at least 1000 nt; and
c) isolating small and large RNA from the supernatant, wherein step c) comprises:
aa) adding at least one alcohol to the supernatant to provide a binding mixture which comprises the alcohol in a concentration ≥40%, ≥45% or ≥50% and wherein the binding mixture additionally comprises a chaotropic salt;

bb) binding total RNA contained in the binding mixture to a silicon containing nucleic acid binding solid phase, wherein after step bb), at least large and small RNA is bound to the solid phase;
cc) washing the bound RNA; and
dd) eluting RNA from the solid phase.

As described above, preferably, a precipitation buffer is added in step a) which comprises the metal cation precipitant in form of a dissolved salt, the organic solvent and the buffering agent in suitable concentrations and with a suitable pH to provide the defined precipitation mixture.

The term "sample" is used herein in a broad sense and is intended to include a variety of sources that contain nucleic acids. The sample may be a biological sample but the term also includes other, e.g. artificial samples which comprise RNA. Exemplary samples include, but are not limited to, tissues, including but not limited to, liver, spleen, kidney, lung, intestine, brain, heart, muscle, fat, pancreas, cell cultures, body fluids in general; whole blood; serum; plasma; red blood cells; white blood cells; buffy coat, tumor cells, fetal cells, host and graft cells; swabs, including but not limited to buccal swabs, throat swabs, vaginal swabs, urethral swabs, cervical swabs, throat swabs, rectal swabs, lesion swabs, abcess swabs, nasopharyngeal swabs, and the like; urine; sputum; saliva; semen; lymphatic fluid; liquor; amniotic fluid; cerebrospinal fluid; peritoneal effusions; pleural effusions; fluid from cysts; synovial fluid; vitreous humor; aqueous humor; bursa fluid; eye washes; eye aspirates; pulmonary lavage; lung aspirates; bone marrow aspirates, cells in suspension, as well as lysates, extracts, or materials obtained from any cells and microorganisms and viruses that may be present on or in a sample and the like. Materials obtained from clinical or forensic settings that contain or are suspected to contain RNA are also within the intended meaning of the term sample. Furthermore, the skilled artisan will appreciate that lysates, extracts, or materials or portions thereof obtained from any of the above exemplary samples are also within the scope of the term sample. Preferably, the sample is a biological sample derived from a human, animal, plant, bacteria or fungi. Preferably, the sample is selected from the group consisting of cells, tissue, body fluids such as for example blood, blood products such as buffy coat, plasma and serum, urine, liquor, sputum, stool, CSF and sperm, epithelial swabs, biopsies, bone marrow samples and diverse tissue samples. As described above, the sample is preferably disrupted prior to preparing the precipitation mixture. The method according to the present invention is particularly suitable for isolating RNA from protein-rich samples, such as plasma or serum. As is shown by the examples, the method according to the present invention allows to efficiently isolate small as well as large RNA from respective samples even though no phenol is used during purification.

The method according to the present invention is also suitable to process blood samples in particular blood samples that were stabilized using for example anticoagulants and samples derived from such blood samples such as plasma or serum. Typical anticoagulants that are used for stabilizing blood samples include but are not limited to EDTA and citrate. The method is also suitable for isolating RNA from samples derived from respective stabilized samples such as from plasma or serum samples. Furthermore, RNA can be isolated from serum samples, including serum samples comprising an activator.

The term "nucleic acid" or "nucleic acids" as used herein, in particular refers to a polymer comprising ribonucleosides and/or deoxyribonucleosides that are covalently bonded, typically by phosphodiester linkages between subunits, but in some cases by phosphorothioates, methylphosphonates, and the like. DNA includes, but is not limited to all types of DNA, e.g. gDNA; circular DNA, plasmid DNA and circulating DNA. RNA includes but is not limited to hnRNA; mRNA; extracellular RNA, noncoding RNA (ncRNA), including but not limited to rRNA, tRNA, IncRNA (long non coding RNA), lincRNA (long intergenic non coding RNA), miRNA (micro RNA), siRNA (small interfering RNA), snoRNA (small nucleolar RNA), snRNA (small nuclear RNA) and stRNA (small temporal RNA), piRNA (piwi interacting RNA), tiRNA (transcription initiation RNA), PASR (promoter associated RNA), CUT (cryptic unstable transcripts). Small RNA or the term small RNA species in particular refers to RNA having a chain length of 200 nt or less, 175 nt or less, 150 nt or less, 125 nt or less, 100 nt or less or 75 nt or less and includes but is not limited to miRNA, siRNA, other short interfering nucleic acids, snoRNAs and the like. Large RNA and similar expression as used herein refer to RNA species which have a length of at least 1000 nt such as at least 1250 nt, at least 1500 nt or even larger. Large RNA in particular includes mRNA. In case the RNA is a double-stranded molecule, the chain length indicated as "nt" refers to "bp". The RNA that can be isolated with the present method may of course also be RNA of intermediate size and is e.g. isolated when isolating total RNA from a sample.

As nucleic acid binding solid phase that can be used for binding the nucleic acids such as RNA, any material that is capable of binding the nucleic acid of interest can be used. This includes a variety of materials capable of binding nucleic acids. Exemplary solid phases that can be used in conjunction with the present invention include, but are not limited to, compounds comprising silicon, including but not limited to, silica materials such as silica particles, silica fibres, glass fibres, silicon dioxide, diatomaceous earth, glass, alkylsilica, aluminum silicate, and borosilicate; nitrocellulose; diazotized paper; hydroxyapatite (also referred to as hydroxyl apatite); nylon; metal oxides; minerals, zirconia; alumina; polymeric supports, organic polymers, diethylaminoethyl- and triethylaminoethyl-derivatized supports, hydrophobic chromatography resins and the like. The term solid phase is not intended to imply any limitation regarding its form or design. Thus, the term solid phase encompasses appropriate materials that are porous or non-porous, permeable or impermeable, including but not limited to membranes, filters, sheets, particles, magnetic particles, beads, gels, powders, fibers and the like. According to one embodiment, a solid phase functionalized with anion exchange ligands is used in order to bind the nucleic acid of interest from the protein-depleted supernatant. E.g. a column or particles such as magnetic particles functionalized with anion exchange ligands may be used. According to another embodiment, the surface of the solid phase such as e.g. a silica solid phase is not modified and is, e.g., not modified with functional groups.

Particularly preferred is the use of silicon containing materials such as silica and polysilicic acid materials, borosilicates, silicates and anorganic glasses as solid phase. Here, the solid phase preferably provides a silica surface for interaction with the RNA which may be bound by precipitation and/or adsorption. The term "silica surface" as used herein includes surfaces comprising or consisting of silicon dioxide and/or other silicon oxides, diatomaceous earth, glass, zeolithe, bentonite, alkylsilica, aluminum silicate and borosilicate. The silica surface is preferably unmodified. Therefore, the surface is not modified with nucleic acid binding ligands or other nucleic acid binding groups. E.g., the solid phase does not carry any ligands at its binding surface that comprise ion exchange groups, in particular, the surface of the solid phase is not modified with functional ligands. In particular, it is not modified with ligands comprising anionic or cationic exchange groups such as e.g. amine groups or carboxyl groups. According to one embodiment, the silica surface does not comprise any functional groups besides its silanol groups or other oxidized forms of silicon, like oxides. Exemplary solid phases that can be used in conjunction with the present invention include, but are not limited to, solid phases comprising a silica surface, including but not limited to, silica particles, silica fibres, glass materials such as e.g. glass powder, glass fibres, glass particles or controlled pore glass, silicon dioxide, glass or silica in particulate form such as powder, beads or frits. According to the present invention, the use of a column based solid phase or the use of particles, in particular magnetic particles, is preferred.

Silica based nucleic acid isolation methods are broadly used in the prior art and work particularly well when isolating RNA, including small RNA using a high alcohol concentrations for binding, preferably in combination with at least one chaotropic salt.

According to one embodiment, silica particles are used that may have the form of beads. Preferably, said particles have a size of about 0.02 to 30 µm, more preferred 0.05 to 15 µm and most preferred of 0.1 to 10 µm. To ease the processing of the nucleic acid binding solid phase, preferably magnetic silica particles are used. Magnetic particles respond to a magnetic field. The magnetic silica particles may e.g. be ferrimagnetic, ferromagnetic, paramagnetic or superparamagnetic. Suitable magnetic silica particles are for example described in WO 01/71732, WO 2004/003231 and WO 2003/004150. Other magnetic silica particles are also known from the prior art and are e.g. described in WO 98/31840, WO 98/31461, EP 1 260 595, WO 96/41811 and EP 0 343 934 and also include for example magnetic silica glass particles. The use of magnetic particles is convenient, because the magnetic particles including the bound RNA can be processed easily by the aid of a magnetic field, e.g. by using a permanent magnet. This embodiment is compatible with established robotic systems capable of processing magnetic particles. Here, different robotic systems exist in the prior art that can be used in conjunction with the present invention to process the magnetic particles to which nucleic acids were bound. According to one embodiment, magnetic particles are collected at the bottom or the side of a reaction vessel and the remaining liquid sample is removed from the reaction vessel, leaving behind the collected magnetic particles to which the nucleic acids are bound. Removal of the remaining sample can occur by decantation or aspiration. Such systems are well known in the prior art and thus need no detailed description here. In an alternative system that is known for processing magnetic particles the magnet which is usually covered by a cover or envelope plunges into the reaction vessel to collect the magnetic particles. As respective systems are well-known in the prior art and are also commercially available (e.g. QIASYMPHONY®; QIAGEN), they do not need any detailed description here. In a further alternative system that is known for processing magnetic particles, the sample comprising the magnetic particles can be aspirated into a pipette tip and the magnetic particles can be collected in the pipette tip by applying a magnet e.g. to the side of the pipette tip. The remaining sample can then be released from the pipette tip while the collected magnet particles which carry the bound nucleic acids remain due to the magnet in the pipette tip. The collected magnetic particles can then be processed further. Such systems are also well-known in the prior art and are also commercially available (e.g. BioRobot EZ1, QIAGEN) and thus, do not need any detailed description here.

According to a preferred embodiment, a column based nucleic acid isolation procedure is performed, wherein the solid phase is comprised in a column. The term "column" as used herein in particular describes a container having at least two openings. Thereby, a solution and/or sample can pass through said column. The term "column" in particular does not imply any restrictions with respect to the shape of the container which can be e.g. round or angular and preferably is cylindrical. However, also other shapes can be used, in particular when using multi-columns. The column comprises the solid phase that is used for RNA binding. Said solid phase comprised in the column should allow the passage of a solution, respectively the binding mixture when applied to the column. This means that if e.g. a centrifuge force is applied to the column, a solution and/or the binding mixture is enabled to pass through the column in direction of the centrifuge force. As discussed above, when using a respective column based RNA isolation procedure, the binding mixture is usually passed through the column, e.g. assisted by centrifugation or vacuum, and the RNA molecules bind to the comprised solid phase during said passage. Which RNA species (small and/or large RNA) is bound depends on the used binding conditions. The column can be used in a single format or in a multi-format. Such multi-columns having a similar format as multi-well plates and which comprise a solid phase such as a silica membrane or glass fibres, are well-known in the prior art and are also commercially available. Preferably, the column is a spin column.

Preferably, a RNA binding membrane or RNA binding fibres are used as solid phase. Examples include but are not limited to silica membranes, glass fibre membranes or filters providing a silicon containing surface for RNA binding. Preferably, the membrane is porous. As is shown by the examples, using a solid phase comprised in a column has several advantages. The use of columns such as spin columns is widely established for RNA purification, and thus, the use of columns is very convenient for the user. Column based methods are also fast and, furthermore, automated systems exist that allow the automated processing of the samples (see e.g. QIAcube, QIAGEN). Thereby, tedious manual handling procedures can be avoided. Furthermore, using a spin column based approach for isolating RNA has the advantage that there is no risk of carryover of potentially inhibitory components from the washing solutions (such as e.g. alcohol) or beads. It is preferred to use a membrane or fibres as solid phase which comprise or consist of silica in the column. Suitable and preferred silica based materials which provide a silica surface suitable for RNA binding were also described above. A further common solid phase comprised in a column is a fill of silica particles, or a layer of a silica material (e.g. a silica gel). E.g. the silica particles can be arranged as a layer on an inert filter or membrane, thereby forming a RNA binding solid phase. To alleviate the passage of the binding mixture through the solid phase comprised in the column, suitable means can be used such as e.g. centrifugation or the use of a pressure difference-generating apparatus which e.g. presses the sample through the column, respectively the solid phase or sucks it through the solid phase by applying a vacuum. Respective means are well known in the prior art and thus need no further description here.

The above described nucleic acid binding solid phases are generally also suitable for binding DNA as is known to the skilled person.

B. Method for Providing a Protein-Depleted Supernatant

According to a second aspect, a phenol-free method for providing a protein depleted supernatant from a sample is provided, said method comprising the following steps:
  a) preparing a precipitation mixture by adding at least one metal cation precipitant and at least one organic solvent selected from aprotic polar solvents and protic solvents to the sample, wherein the precipitation mixture
    i) comprises the metal cation precipitant;
    ii) comprises the organic solvent in a concentration of 15% or less;
    iii) comprises at least one buffering agent; and
    iv) has an acidic pH value,
    and precipitating proteins; and
  b) separating the precipitate from the supernatant, wherein the obtained supernatant comprises small RNA having a length of less than 200 nt and large RNA having a length of at least 1000 nt.

Details with respect to the individual steps a) and b), suitable types and concentrations of the metal cation precipitant and the organic solvent as well as different sample types from which the protein-depleted supernatant can be prepared were described above in conjunction with the method according to the first aspect and in the claims and it is referred to the respective disclosure which also applies here. As described, the sample in step a) is according to one embodiment a disrupted sample. Sample disruption may occur prior to or at the same time when the precipitation mixture is prepared. According to one embodiment, the method according to the second aspect comprises a step x) wherein the sample is disrupted prior to step a). Details of such disruption step were described above and it is referred to the above disclosure. Preferably, a precipitation buffer is added in step a) which comprises the metal cation precipitant, the organic solvent and a buffering agent in order to establish the precipitation conditions in the precipitation mixture. Details of said precipitation buffer were described above. E.g., a precipitation buffer according to the third aspect as it is also defined in the claims can be used for that purpose. The precipitation buffer is preferably added to the disrupted sample.

The method provides a protein depleted supernatant which in contrast to prior art methods comprises small as well as large RNA (and RNA of intermediate size) and in embodiments also high molecular weight nucleic acids such as genomic DNA. Details were described above and it is referred to the above disclosure. The nucleic acid species of interest can then be isolated from the protein depleted supernatant using various nucleic acid isolation methods. The used method will also depend on the target nucleic acid of interest. Exemplary, non-limiting embodiments suitable for isolating RNA as well as DNA were described above and it is referred to the above disclosure.

C. Precipitation Buffer

According to a third aspect, a precipitation buffer is provided comprising:
  a) at least one metal cation precipitant;
  b) at least one organic solvent selected from aprotic polar solvents and protic solvents; and
  c) at least one buffering agent;
wherein the precipitation buffer has a pH value that lies in a range of 3 to 5.5.

The respective precipitation buffer can be advantageously used in order to precipitate proteins from various biological samples, in particular disrupted biological samples. Therefore, it may be specifically used in the methods according to the first and second aspect of the present invention in order to precipitate proteins. Details of said precipitation buffer were already described above in conjunction with the method according to the first aspect and it is referred to the respective disclosure which also applies here. Non-limiting embodiments are again described briefly in the following.

The metal cation precipitant may be comprised in the precipitation buffer in form of a dissolved salt at a concentration selected from 0.75M to 3 M, 1M to 2.8M, 1.25M to 2.7M, 1.5M to 2.6M or 1.7M to 2.5M. E.g. halogenide salts such as chloride salts may be used. In case two or more metal cation precipitants are comprised, these concentrations refer according to one embodiment to the overall concentration of the comprised metal cation precipitants. As is demonstrated by the examples, using a precipitation buffer that comprises the metal cation precipitant in a respective concentration provides good results. Suitable metal cation precipitants were described above, preferably the metal cation precipitant is selected from $Zn^{2+}$ and $Al^{3+}$, $Zn^{2+}$ is particularly preferred. It can be comprised in the precipitation buffer as zinc chloride.

The precipitation buffer may comprise the organic solvent selected from aprotic polar solvents and protic solvents in a concentration selected from 13% to 65%, 20% to 63%, 25% to 62.5%, 30% to 60%, 33% to 57.5%, 37.5% to 55% or 40% to 52.5%. In case two or more respective organic solvents are comprised in the precipitation buffer, these concentrations refer according to one embodiment to the overall concentration of the comprised organic solvents. Suitable examples of suitable organic solvents selected from aprotic polar solvents and protic solvents were described above in conjunction with the method according to the first aspect and are also evident from the examples. The organic solvent is miscible in water. Preferably, the organic solvent is an aprotic polar solvent, such as DMSO. Furthermore, protic organic solvents can be used, such as water-miscible alcohols. Preferably, the protic organic solvent is a lower aliphatic alcohol, such as e.g. methanol, ethanol and isopropanol.

The precipitation buffer may have a pH value that is selected from 3 to 5.5, 3 to 5.25, 3.25 to 5, 3.25 to 4.75, 3.5 to 4.5 and 3.75 to 4.4. Particularly preferred is a pH in the range of 3 to 5, preferably 3.25 to 4.75, more preferred 3.5 to 4.5 or 3.75 to 4.4. As is demonstrated by the examples, using a precipitation buffer that has a respective acidic pH value provides advantageous results, in particular when processing protein rich samples such as plasma or serum.

To maintain the acidic pH value, the precipitation buffer comprises at least one buffering agent. As is demonstrated by the examples, different buffering agents may be used. Also combinations of buffering agents may be used. According to one embodiment, the buffering agent is or is derived from a carboxylic acid. Carboxylic acids include mono-, di- or tri carboxylic acids. Preferably, the buffering agent is acetic acid or citric acid, respectively is an acetate or citrate. As is demonstrated by the examples, acetate and citrate can be added in form of different salts. Furthermore, phosphate buffers such as PIPPS can be used. According to one embodiment, the precipitation buffer comprises the buffering agent in a concentration selected from 300 mM to 2M, 400 mM to 1.75M, 450 mM to 1.5M, 500 mM to 1.4M, 550 mM to 1.3M and 600 mM to 1.25M. Particularly preferred are carboxylic acid salts such as acetate or citrate salts, e.g. alkali metal salts which may be used in the before mentioned concentration ranges. Particularly preferred is a concentration that lies in the range of 550 mM to 1.3M, 600 mM to 1.25M or 650 mM to 1.2M. In case two or more buffering agents are used, the respective concentrations refer according to one embodiment to the overall concentration of the buffering agent in the precipitation buffer.

According to one embodiment, the precipitation buffer aa) comprises $Zn^{2+}$ or $Al^{3+}$, preferably $Zn^{2+}$, as metal cation precipitant in form of a dissolved salt in a concentration selected from 1.25M to 2.8M, 1.5M to 2.6M or 1.7M to 2.5M;

bb) comprises the organic solvent, which preferably is an aprotic polar organic solvent, in a concentration selected from 13% to 65%, 20% to 63%, 25% to 62.5%, 30% to 60%, 33% to 57.5%, 37.5% to 55% or 40% to 52.5%; and cc) has a pH value that lies in a range of 3.25 to 4.75 or 3.4 to 4.5.

As described above $Zn^{2+}$ is preferred and can be comprised e.g. as zinc chloride.

The precipitation buffer according to the third aspect may also be included in a kit. Therefore, the present disclosure also provides a kit. The kit is for isolating a nucleic acid, preferably at least RNA, from a sample. The kit comprises according to one embodiment all reagents that are necessary for isolating the nucleic acid which preferably is at least RNA. According to one embodiment, such kit comprises the precipitation buffer according to the third aspect and one or more of the following components:

at least one disruption reagent;
at least one nucleic acid binding solid phase;
at least one binding solution;
at least one washing solution; and/or
at least one elution solution.

The kit comprises according to one embodiment the precipitation buffer, a disruption reagent comprising a chaotropic salt and a nucleic acid binding solid phase. Suitable embodiments for respective disruption reagents and nucleic acid binding solid phases were described above in conjunction with the method according to the first aspect and it is referred to the above disclosure which also applies here. The kit may further comprise a binding solution.

The binding solution may comprise or consist of an alcohol suitable to promote binding of a nucleic acid such as preferably RNA to a nucleic acid binding solid phase. Suitable alcohols were described above, preferred are ethanol and isopropanol. This embodiment is e.g. suitable if a silicon containing material is used as nucleic acid binding solid phase. The binding solution may comprise a chaotropic agent such as preferably a chaotropic salt. This is particularly advantageous is case the disruption buffer does not comprise a chaotropic salt.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

As used in the subject specification and claims, the singular forms "a", "an" and "the" include plural aspects unless the context clearly dictates otherwise. Thus, for example, reference to "a metal cation precipitant" includes a single type of metal cation precipitant, as well as two or more metal cation precipitants. Likewise, reference to an "alcohol", an "organic solvent", a "chaotropic salt", a "buffering agent" and the like includes single entities and combinations of two or more of such entities. Reference to "the disclosure" and "the invention" and the like includes single or multiple aspects taught herein; and so forth. Aspects taught herein are encompassed by the term "invention".

The term "solution" as used herein in particular refers to a liquid composition, preferably an aqueous composition. It may be a homogenous mixture of only one phase but it is also within the scope of the present invention that a solution comprises solid constituents such as e.g. precipitates.

According to one embodiment, subject matter described herein as comprising certain steps in the case of methods or as comprising certain ingredients in the case of compositions, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

EXAMPLES

I. Materials and Methods

If not stated otherwise, total RNA was isolated from serum, plasma or tissue according to the following standard protocol:

1. Materials

Precipitation buffer XP (45% (v/v) DMSO; $ZnCl_2$ (1.909 M); NaOAc; pH 4-4.5)

Silica columns (RNeasy® MinElute® spin columns)
Collection tubes (1.5 ml and 2 ml)
Washing buffer RWT (QIAGEN; contains GTC, 2 volumes ethanol (96%-100%) are added to the buffer concentrate RWT prior to use)
Washing buffer RPE (QIAGEN; 4 volumes ethanol (96%-100%) are added to the buffer concentrate RPE prior to use)
Lysis buffer RLT Plus (QIAGEN; contains a chaotropic salt and detergents)
RNase-free water
Ce_miR-39_1 miScript® primer assay 2. Total RNA Isolation
2.1. Manual Procedure
Sample Preparation 120 µl lysis buffer (RLT Plus, QIAGEN) is added to 200 µl sample such as serum or plasma. The lysis mixture is vortexed for 5 seconds and incubated 3 min at room temperature to disrupt the sample.

Protein Precipitation

95 µl precipitation buffer XP is added to the disrupted sample and vortexed for 3 seconds. Optionally, 3.5 µl miRNeasy serum spike-in control ($1.6 \times 10^8$ copies/µl) is added and vortexed again 3 seconds. The sample is then incubated 3 min on ice. Optionally, the samples may also be stored for several hours at 4° C. The obtained precipitate is removed by centrifugation at >11.000 rpm for 3 min. The nucleic acid containing supernatant is transferred to a new collection tube.

RNA Binding 1 volume (360 µl) alcohol (e.g. isopropanol) is added to the supernatant and the binding mixture is vortexed for 5 seconds. The binding mixture is then applied to the silica spin column and incubated at room temperature for 2 min. Afterwards, the columns are centrifuged for 30 seconds at >11.000 rpm.

Washing Steps

To further purify the bound RNA, several washing steps were performed: 700 µl RWT, centrifugation for 15 seconds at >8000×g, discard flow through; 800 µl RPE, centrifugation for 15 seconds at >8000×g, discard flow through; 700 µl RPE, centrifugation for 15 seconds at >8000×g, discard flow through. Finally, 300 µl 100% ethanol is added to the column and centrifuged for 2 min at >8000×g; the flow through is discarded. The column with the washed RNA is then transferred to a new 2 ml collection tube. The column with opened lid is then centrifuged for 5 min at maximum rpm to remove remaining traces of ethanol.

Elution

The column is transferred to a new 1.5 ml reaction vessel. 20 µl RNase-free water is applied to the middle of the column. The column is closed and centrifuged for 1 min at maximum rpm. Optionally, a second elution step can be performed, e.g. using the already obtained eluate.

2.2. Multiwell (96) Approach

The manual protocol can also be performed processing multiple samples at the same time, using 96 well-plates on a BioRobot Universal robotic system or e.g. the QIAcube HT system. The sample preparation may be performed in a CMTR (Collection micro tube rack) block:

Sample Preparation

200 µl serum or plasma is added to a CMTR block. 120 µl lysis buffer (RLT Plus, QIAGEN) is added and mixed. For lysis, the lysis mixture is incubated for 3 min at room temperature.

Protein Precipitation

95 µl precipitation buffer XP is added to the lysis mixture and the samples are mixed. Optionally, 3.5 µl miRNeasy serum spike-in control ($1.6 \times 10^8$ copies/µl) is added and mixed. As described above, it is also possible to store the samples at this stage for several hours at 4° C. The precipitate is removed by centrifugation at 4° C. at >5.000 rpm for 5 minutes. The CMTR block is than further processed in the BioRobot Universal system. The further BioRobot protocol corresponds to the existing miRNeasy BioRobot protocol for serum/plasma samples. The only adaption is the volume of the supernatant that is obtained from the samples. The RNA isolation is performed using an RNeasy 96 plate. The washing steps correspond to the ones described for the manual preparation. The elution volume is 2×55 µl.

II. Experiments

Example 1: Isolation of Total RNA Including miRNA from Serum and Plasma Using the BioRobot Universal Protocol The efficiency of the method according to the invention is demonstrated using different sample types. As sample material, different human serum and plasma samples (pooled) were used (see Table 1):

| Name/sample type | Collection tube | Storage | Pooled sample |
| --- | --- | --- | --- |
| Serum (neutral) | Without clot activator | 1 month (−20° C.) | Mixture from 6 donors |
| Serum (activator) | With clot activator | 1 month (−20° C.) | Mixture from 6 donors |
| Serum 2005 | Unknown | ~8 years (−20° C.) | Mixture from 2 donors |
| Plasma (EDTA) | EDTA | 1 month (−20° C.) | Mixture from 6 donors |
| Plasma (citrate) | Sodium citrate | 1 month (−20° C.) | Mixture from 6 donors |

RNA was isolated from the same pooled sample using 1) the established QIAzol preparation method (miRNeasy for plasma/serum; involves the use of phenol) or 2) the phenol-free method according to the invention. As RNA was obtained from the same pooled sample, the RNA isolation efficiency of the methods can be directly compared.

Figure 2:
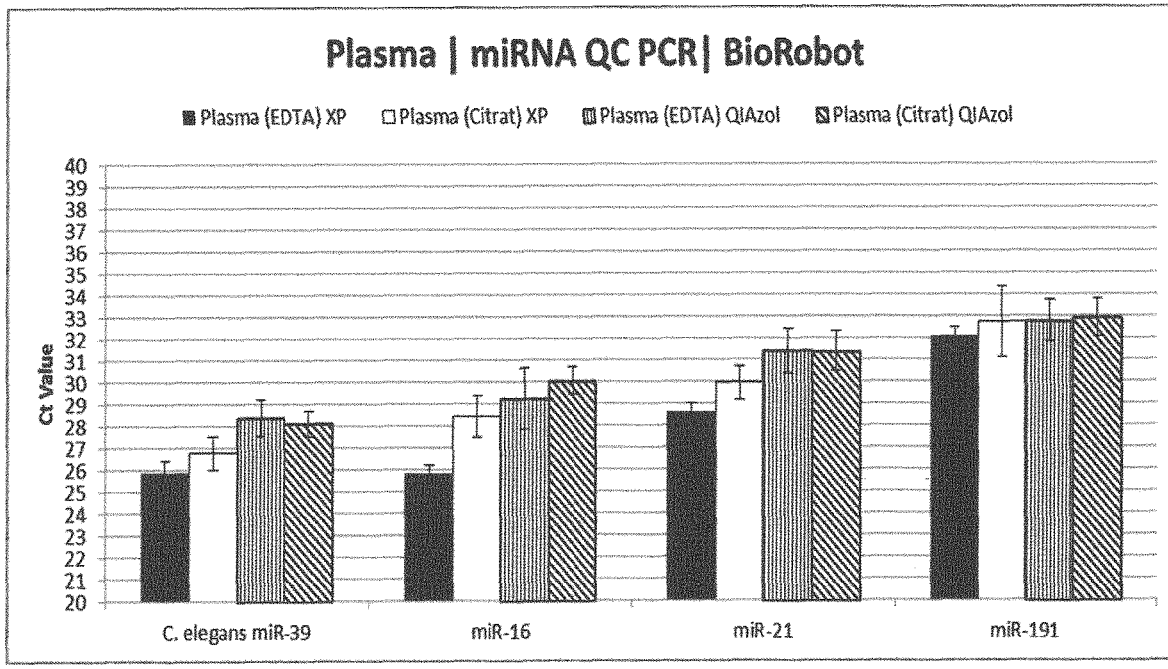

From each pooled sample, 8 replicates were processed with both methods on the BioRobot Universal system. 6 µl of each eluate were subsequently analyzed using the miScript miRNA PCR array miRNA QC (MIHS-989Z). FIG. 1 (serum) and FIG. 2 (plasma) show the Ct values of three quantified miRNAs (miR-16, miR-21 and miR-191) and the spike-in control Cel-miR-39. The method according to the invention achieved in most cases better results (i.e. lower Ct values) than the established prior art isolation protocol (miRNeasy). Therefore, the phenol-free method according to the present invention provides equivalent or even better results than the established phenol-based RNA isolation method.

Example 2: Spectrum of Isolated miRNAs

Figure 3:
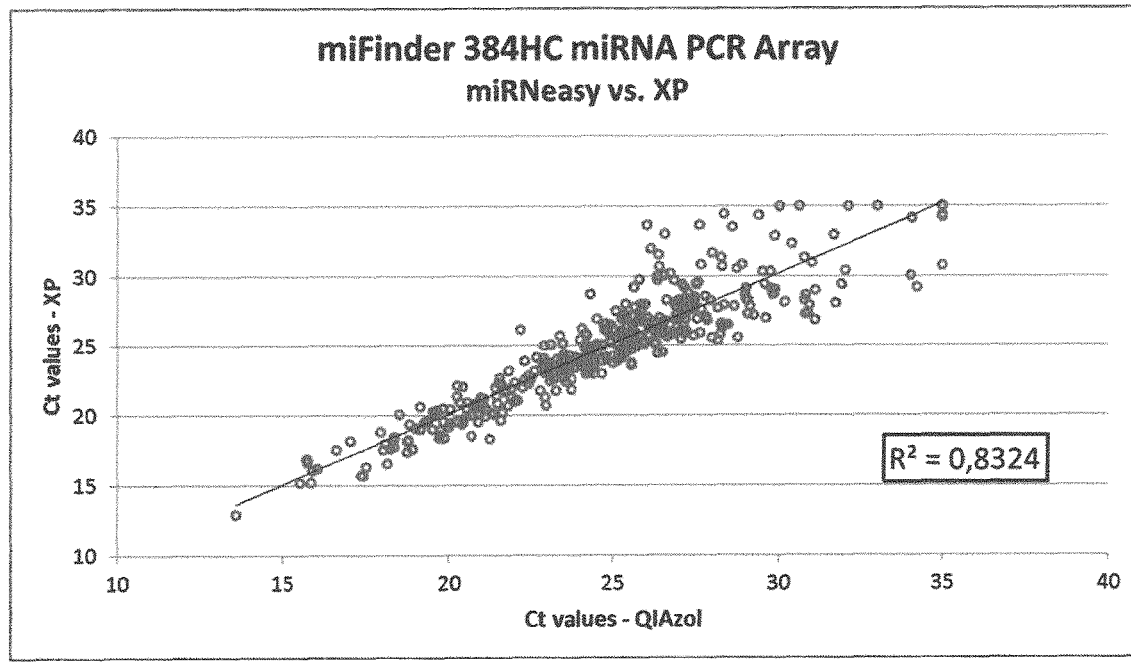
FIG. 3: Shown are the qRT-PCR results of a "human miFinder 384HC miRNA PCR array" analysis. 6 (miRNeasy) and 8 (precipitation XP) replicates of miRNA isolated from the same sample material were analyzed. This PCR assay addresses 372 miRNAs. The mean, normalized Ct-values smaller than 35 were directly plotted against each other. The shown trend line follows the formula y=1.0051× and the coefficient of determination is $R^2$=83.2%.

It was analyzed whether the method according to the present invention allows to isolate a comparative spectrum of miRNAs from the same sample as the established miRNeasy isolation protocol. RNA was manually isolated from a pooled serum sample using either the miRNeasy serum/plasma kit (6 replicates) or the method according to the present invention (8 replicates). The obtained eluates were analyzed using the "human miFinder 384HC miRNA PCR array". The mean Ct values of the quantified 372 miRNAs and the mean values of both methods were directly plotted against each other in a diagram. The results are shown in FIG. 3. The achieved correlation coefficient of more than 83% shows that the method according to the present invention allows to isolate most of the analyzed miRNAs, abundant as well as rare targets, with comparable efficiency.

Example 3: Influence of the Aprotic Polar Solvent on the miRNA-Isolation

In order to analyze how the aprotic polar organic solvent influences the RNA isolation, RNA was isolated from pooled serum samples (6 donors, collection tube without clot activator) using the above described manual protocol. Besides the standard precipitation buffer XP, modified precipitation buffers without DMSO and hence without an aprotic polar organic solvent were used for comparative purposes. The miRNA isolation efficiency was analyzed using different isopropanol (alcohol) concentrations in the binding mixture as well as different DMSO concentrations. The quantification was performed using the miScript miRNA PCR array miRNA QC (MIHS-989Z).

Table 2 shows the setup of the different precipitation buffers (w/o=without), indicates the DMSO concentration in the precipitation mixture and also indicates the final alcohol (isopropanol) and DMSO concentration in the binding mixture:

| Setup name | Precipitation buffer | DMSO/ precipitation mixture | Isopropanol/ binding mixture | DMSO/ binding mixture |
|---|---|---|---|---|
| XP Standard | XP | 10% | 50% | 6% |
| XP (w/o DMSO); 50% isopropanol | XP without DMSO | 0% | 50% | 0% |
| XP (w/o DMSO); 55% isopropanol | XP without DMSO | 0% | 55% | 0% |
| XP (w/o DMSO); 45% isopropanol + and 10% DMSO | XP without DMSO | 0% | 45% | 10% |

Figure 4:
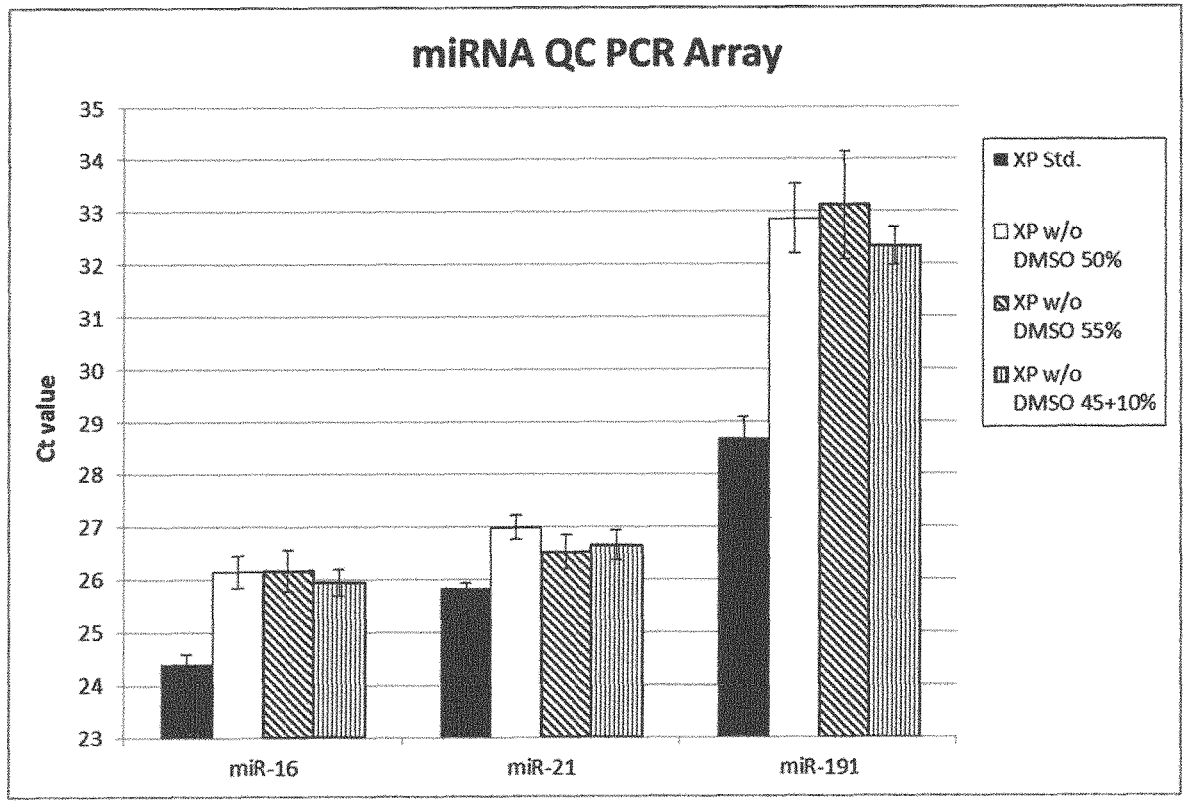
FIG. 4: Shown are the qRT-PCR results of the miScript miRNA QC PCR Array. miRNA contained in the eluates obtained after RNA isolation from serum using different DMSO and isopropanol concentrations during precipitation and subsequent binding were analyzed. Shown are the mean values of 8 replicates for each condition as well as a corresponding standard deviation.

FIG. 4 shows the results. As can be seen, for binding RNA including small RNA to the solid phase, the presence of DMSO in the binding mixture did not play an essential role, because using XP (w/o DMSO) and 50%-55% isopropanol provided in essence the same results as using XP (w/o DMSO) and 45% isopropanol+10% DMSO in the binding mixture (the DMSO was added here after the protein precipitation step). Here, apparently the overall solvent concentration during binding was relevant. However, surprisingly, the obtained results demonstrate that it is important that the aprotic polar solvent (here: DMSO) is already present during the precipitation step and apparently has here a stabilizing effect on the small RNA. As can be seen from the lower CT values, the standard precipitation buffer XP according to the invention (comprising DMSO) provided significantly better results than the other precipitation buffers (not comprising DMSO). Furthermore, as is demonstrated with the buffer XP (w/o DMSO) 45% isopropanol+ 10% DMSO, also the subsequent addition of DMSO after the precipitation step but prior to RNA binding does not improve the results. Without wishing to be bound in theory, besides exerting a stabilization effect on the miRNAs during precipitation it is also possible that protein complexes comprising miRNA are dissolved by the DMSO during the precipitation step and therefore, support the release of the small RNA which can then be recovered more efficiently in the subsequent binding step. This would be congruent with the observation that Ct values of miR-191 were advantageously significantly reduced when using the method according to the present invention compared to methods wherein no DMSO was used during precipitation (see FIG. 4).

Example 4: Influence of the Aprotic Polar Organic Solvent on the Total RNA Isolation The method according to the present invention aims at allowing to isolate small as well as large RNA from a sample, e.g. in form of total RNA. To analyze the isolation efficiency for larger RNA molecules, total RNA was isolated from cell culture. As sample material, a pooled lysate of 4×10$^7$ Jurkat-cells lysed in 8 ml lysis buffer (RLT, QIAGEN) was used. RNA was isolated from 2000 lysate (6 replicates). For comparison, RNA was also isolated using different precipitation based methods according to example 3. In all cases, silica containing columns (RNeasy mini columns) were used and the RNA was eluted using 50 µl RNase free water. As control, RNA was isolated using the RNeasy mini kit (according to the manual) and the miRNeasy serum/plasma kit (QIAzol; according to the manual).

The RNA content of the obtained eluates was analyzed using spectrophotometric measurements (Nanodrop). Additionally, individual samples were analyzed with the Agilent BioAnalyzer and an RNA 6000 chip. The samples "RNeasy", "QIAzol" and "XP" were diluted 1:4 prior to the Agilent analysis. The eluates of the samples isolated without DMSO in the precipitation buffer ("XP 50", XP 55" and "XP 45+10") were analyzed without dilution.

Figure 5:
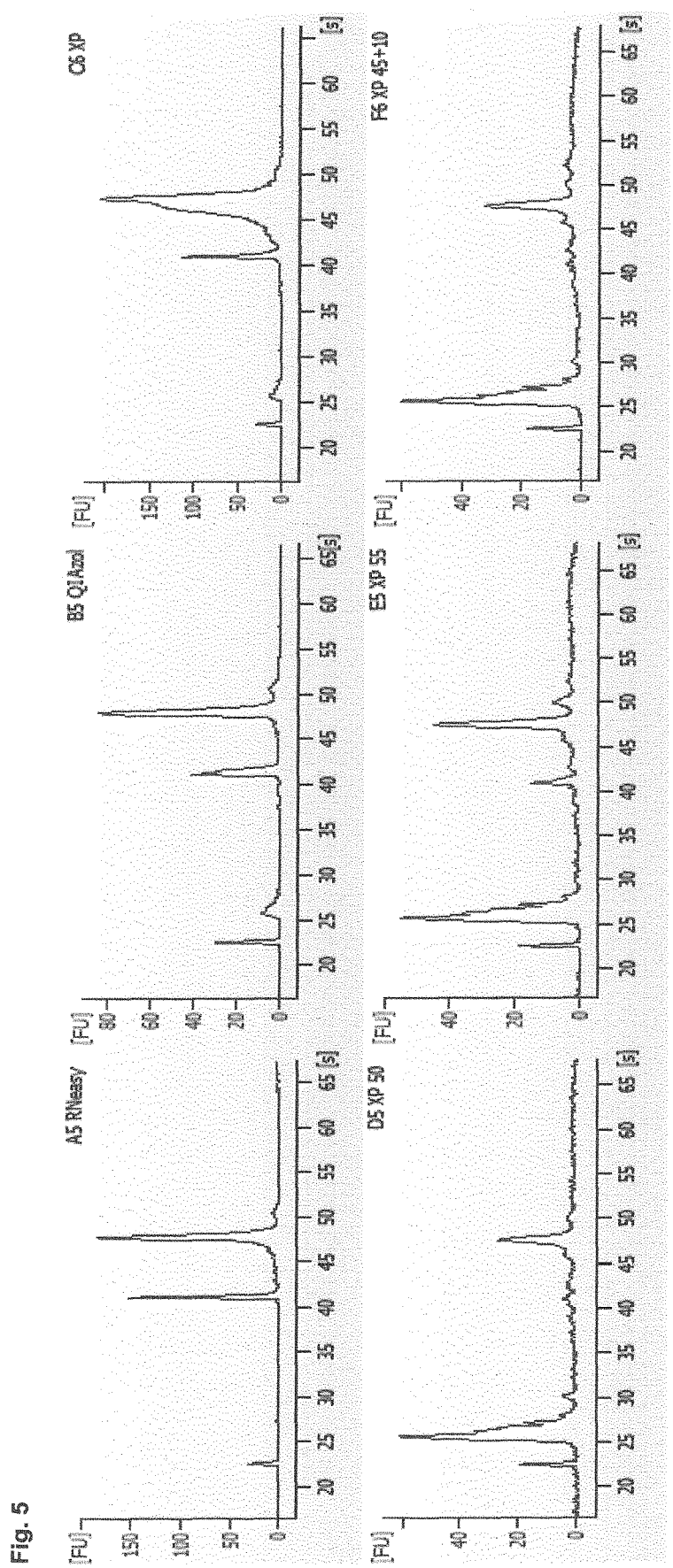
FIG. 5: Shows the analysis of the eluates using an Agilent Bioanalyzer RNA 6000 chip. The samples "RNeasy", "QIAzol" and "XP" were diluted 1:4 with water in advance.

The results are shown in FIG. 5. The eluate obtained from the RNeasy isolation showed as expected a good ratio between 18S and 28S RNA and therefore, efficiently isolated large RNA. However, small RNAs ≤200 nt were in essence missing in the obtained eluates. The eluate obtained using the QIAzol-based miRNeasy isolation procedure showed a lower concentration of RNA, however, the eluate comprised besides large RNA also small RNAs. The eluate obtained with the precipitation based method according to the invention, wherein DMSO is comprised in the precipitation buffer (XP) comprises similar to the RNeasy method significant amounts of 18S and 28S RNA (and therefore large RNA) but additionally comprised small RNAs. The structure of the broad 28S peaks could be attributable to DNA in the eluate or could be a measurement artifact of the Agilent chip. The eluates prepared without DMSO in the precipitation buffer comprised significantly less RNA and additionally, lacked most of the large 18S and 28S RNA. This emphasizes the advantages of including an aprotic polar organic solvent in the precipitation mixture.

Figure 6:
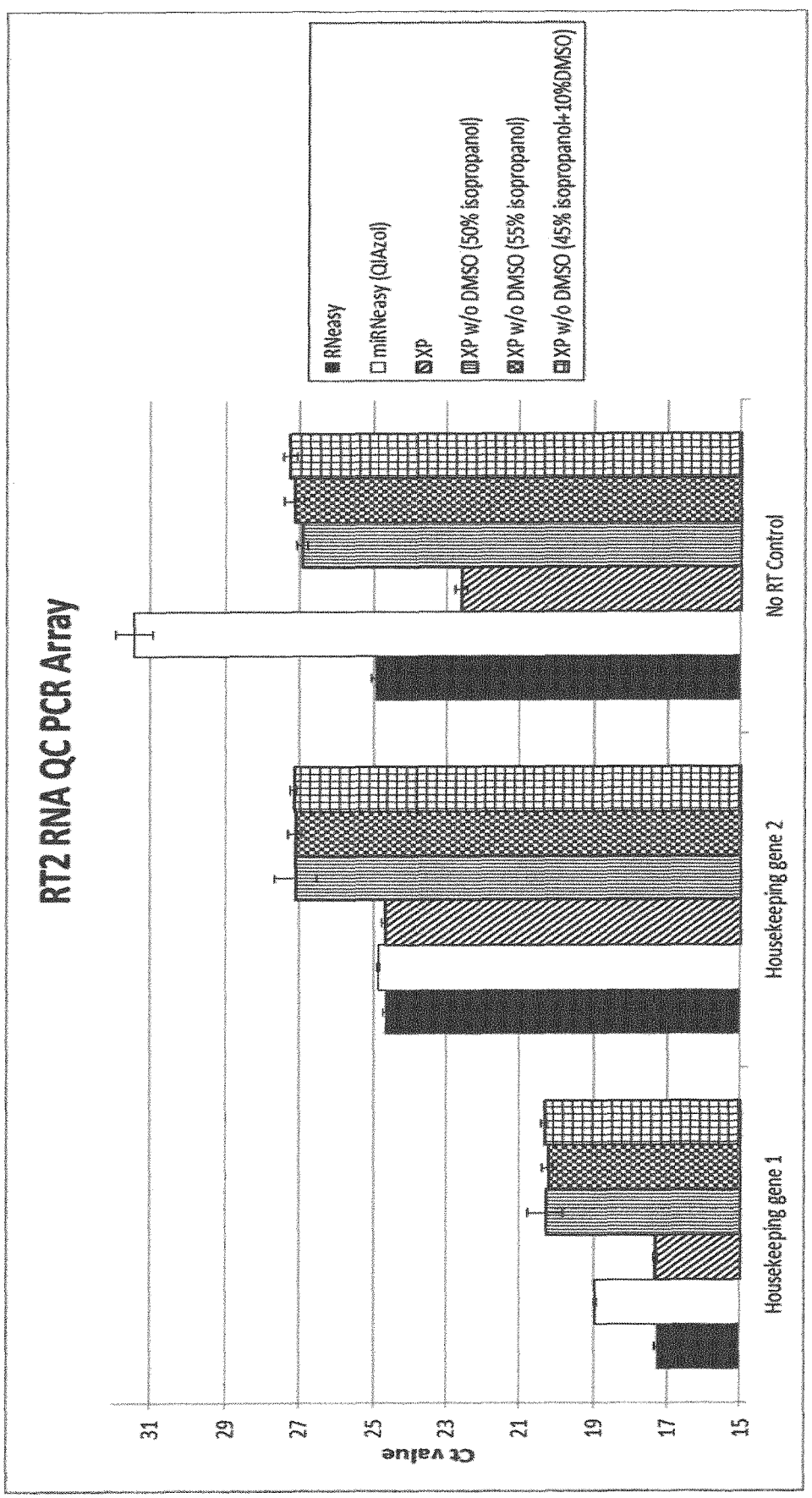
FIGS. 6 and 7: Shows the qRT-PCR results of the $RT^2$ RNA QC PCR arrays (FIG. 6) and the Nanodrop results (FIG. 7). The eluates obtained using different RNA isolation protocols from cell lysates were analyzed. Shown are the obtained Ct-values of the individual samples as well as the corresponding nucleic acid concentration.
Figure 7:
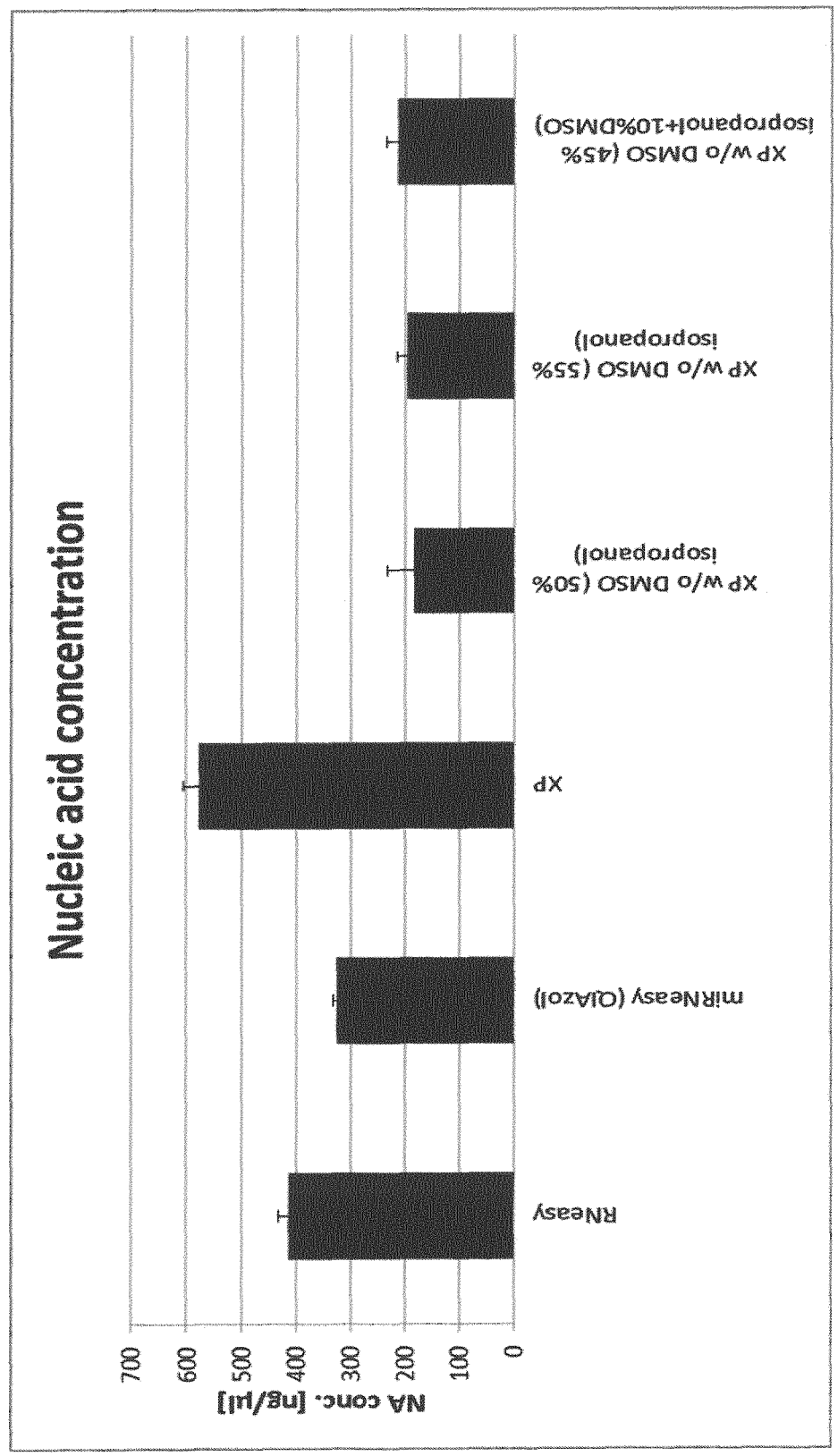

Four eluates of each setup were furthermore analyzed using a RT$^2$ RNA QC PCR array. This array quantifies inter alia the mRNA of two housekeeping genes as well as potentially present gDNA. For a better comparison, FIG. 6 and FIG. 7 also shows the RNA content of the samples that were determined using Nanodrop.

The mRNA content in the eluates (determined based on the two housekeeping genes) of the RNeasy method and the precipitation based method according to the present invention (XP) is substantially the same, which clearly demonstrates that mRNA is in contrast to prior art methods not removed during the protein precipitation step but can be recovered when using the present method. The higher overall amount of nucleic acids in the eluates obtained using the method according to the present invention compared to the RNeasy preparation could be attributable to a higher DNA content, as can be seen from the "no RT control" values. The QIAzol based approach shows the lowest concentration of the housekeeping gene 1. Also the overall nucleic acid content is lower. This is confirmed by the Agilent BioAnalyzer data. As expected, the amount of genomic DNA is the lowest in the QIAzol-based preparation. The three RNA preparations obtained with the precipitation buffers without DMSO showed in comparison worse results (higher Ct values, low overall nucleic acid concentration). With the precipitation buffers without DMSO, the obtained Ct values are 2 to 3 Ct units higher as would be expected based on the contained nucleic acid concentration. Based on the nucleic acid yield (200 ng compared to 600 ng) the maximum difference that would be expected would lie approximately around 1.5 Ct. This demonstrates together with the Agilent analysis the advantage of using an aprotic polar organic solvent such as DMSO in the protein precipitation step. Using an aprotic polar organic solvent during the precipitation step allows the efficient purification of large RNA from the protein-depleted supernatant.

Example 5: miRNA Isolation from Tissue Samples

RNA was also isolated from different tissue samples using the method according to the present invention. For this purpose, rat brain and rat liver was disrupted to provide batch-lysates. C. elegans spike-in control was added directly to the batch lysates. RNA was isolated in parallel from the lysates using either the miRNeasy mini kit (according to the manual) or the precipitation based method according to the present invention. The obtained lysates were homogenized using the TissueRuptor either directly in QIAzol or alternatively, in the lysis buffer RLT plus (including beta-Mercaptoethanol). Overall, approximately 10 mg tissue sample was processed per preparation. Because of the expected high RNA content, RNeasy Mini Spin columns were used instead of RNeasy MinElute columns as solid phase. Elution occurred using 50 µl RNase free water. 6 replicates were prepared per method and tissue type. Additionally, 4 further replicates were prepared per condition, wherein an additional on-column DNase digestion was performed. The eluate from each condition was analyzed subsequently using qRT-PCR analysis. The eluates that were obtained from liver were, however, diluted (1:10) with water in advance due to the high RNA-content.

Figure 8:
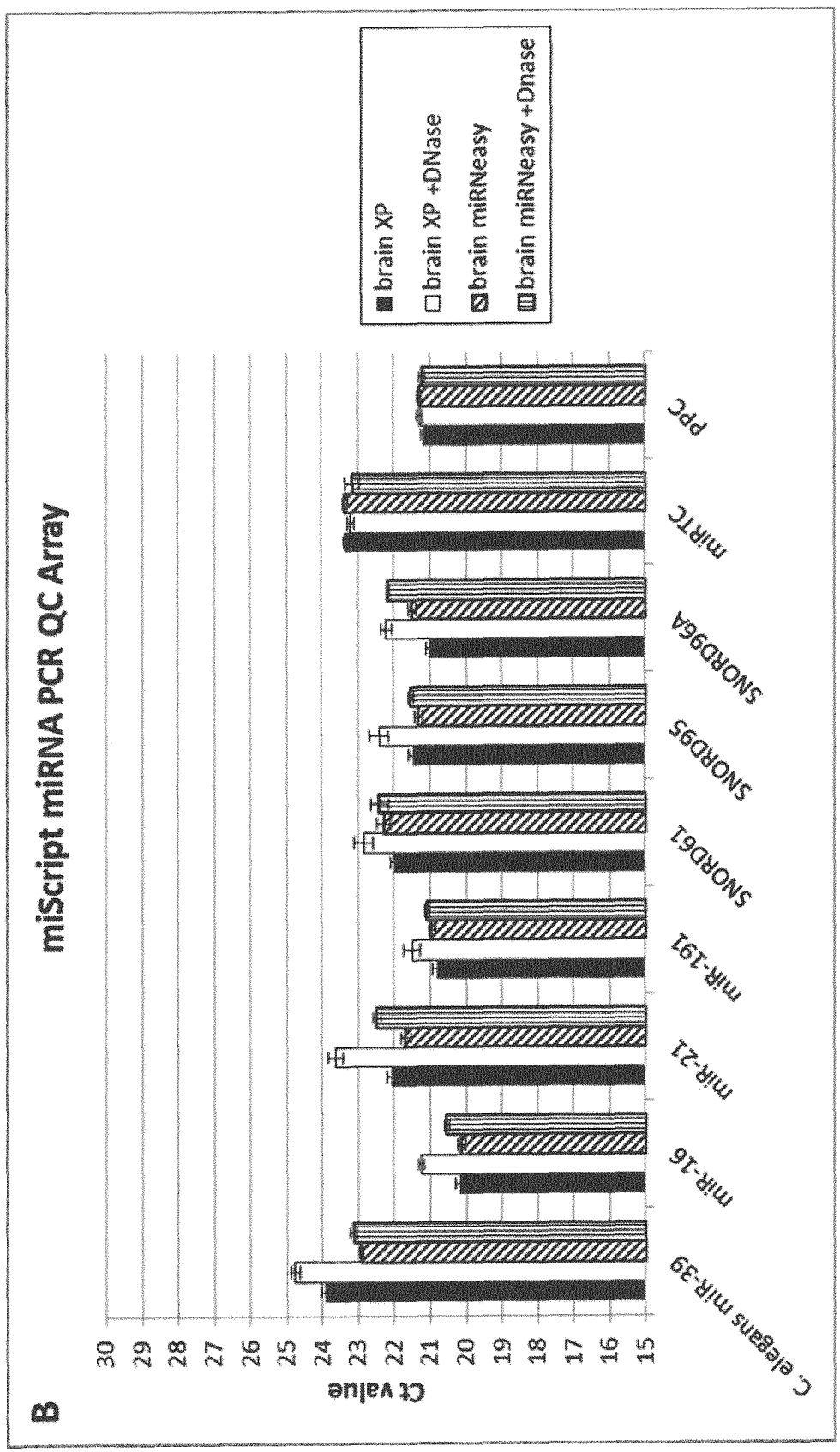
FIGS. 8a and 8b: Shown are the qRT-PCR results of the miScript miRNA QC PCR Array. The same volumes of eluates obtained from different tissue types rat-liver (A) or rat-brain (B) using the protocols "precipitation" (XP) and "miRNeasy" with our without additional on-column DNase digestion were analyzed. Shown are the mean values obtained from 4 replicates as well as the standard deviation.

The results are shown in FIG. 8. As can be seen, basically the same Ct values were obtained during qRT-PCR analysis for the analyzed miRNAs (miR-16, miR-21 and miR-191) as well as for the three analyzed snoRNAs (SNORD61, SNORD95, SNORD96a) using the established QIAzol based method or the method according to the present invention. This demonstrates that both methods achieve a similar small RNA isolation efficiency, even if processing different sample types. The observed differences in the isolation efficiency of the spike-in control *C. elegans* miR-39 is probably attributable to different stabilities of the added spike-in controls in the lysates. The performed DNAse digestion only contributes to a minor extent to the quality of the performed qRT-PCR analysis. This could be the result of the changed washing protocol that was used when performing a DNase digest (2×350 µl RWT buffer instead of 1×700 µl RWT) and potentially be attributable to the longer standing times of the columns during the on-column DNase digestion step. However, generally, the performance of a DNase digestion is possible, however, it is not necessary in particular when performing a qRT-PCR analysis using the miScript miRNA PCR system.

Example 6: The Role of the Organic Solvent Used During Precipitation

As described above, an aprotic polar organic solvent such as DMSO contributes to the stabilization of small and large RNA in the isolation method according to the present invention, wherein proteins are precipitated prior to isolating RNA. In example 6, it was confirmed that corresponding results are likewise achieved when using other aprotic polar organic solvents or protic organic solvents such as ethanol and isopropanol. Water was tested for comparison. The following solvents were tested:

| Solvent | Solvent Class |
|---|---|
| Dimethylsulfoxide (DMSO) | Aprotic, polar |
| Acetone | |
| Tetrahydrofurane (THF) | |
| Dioxane | |
| Dimethylformamide (DMF) | |
| Acetonitril | |
| 1-methyl-2-pyrolidone (NMP) | |
| Isopropanol | Protic |
| Ethanol | |
| Water (not an organic solvent) | |

Figure 9:
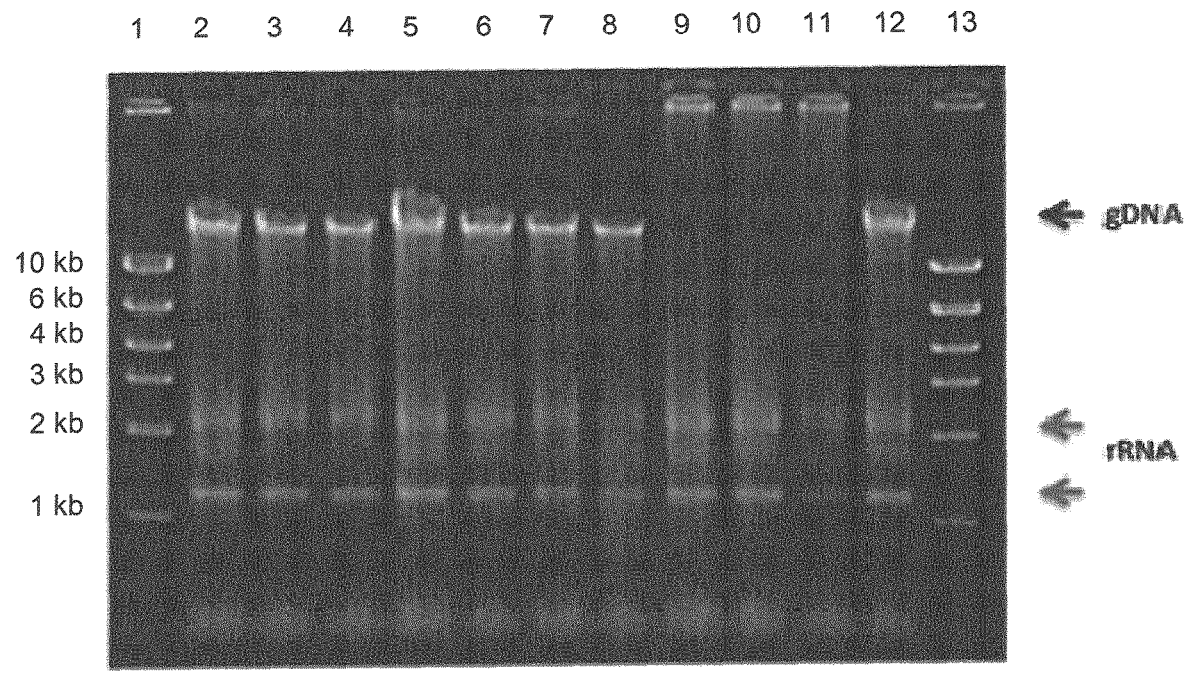
FIG. 9: Shown is a gelelectrophoretic separation of the nucleic acid containing eluates, which were obtained using the precipitation based method according to the invention and using different water-miscible organic solvents besides DMSO or water. 1.5 µl eluate was separated for 1 hour in a non-denaturing agarose gel (0.8%) with 120 V. The shown marker is a DNA marker. Therefore, the indicated kb values are not directly transferable to the shown rRNA bands, which in general have a higher molecular weight.

Total nucleic acids were prepared from cell lysates (1×10$^6$ Jurkat cells per sample, lysed in 200 µl RLT buffer) using different precipitation buffer variants that contained the indicated different organic solvents. 1.5 µl aliquots of the obtained eluates were separated on a 0.8% agarose gel. The results are shown in FIG. 9.

As can be seen, with the tested aprotic, polar organic solvents, not only small RNA but also large RNA could be isolated successfully from the protein-depleted supernatant. Additionally, high molecular weight DNA could be isolated. Therefore, the aprotic polar organic solvents tested allowed to isolate small RNA, large RNA and if desired also genomic DNA from the protein-depleted supernatant. Using the protic organic solvents isopropanol and ethanol, likewise small as well as large RNA (as can be seen from the isolated rRNA) could be isolated. Therefore, using the precipitation conditions according to the present invention did not result in that large RNA was lost during the protein precipitation step as it is, however, the case with prior art methods. However, high molecular weight nucleic acids such as genomic DNA were apparently lost either during the protein precipitation step or during the subsequent isolation when using ethanol or isopropanol as organic solvent during the precipitation step. Furthermore, using water instead does not lead to acceptable results, because the yield of 28S and 18S rRNA is significantly reduced.

The results were confirmed by several replicates. Additionally, different miRNAs were detected in the eluates to analyse the small RNA yield. The following tables show the results and the standard deviation from two replicates:

| | Acetone | Acetonitrile | Dioxane | DMF | DMSO | NMP | THF | EtOH | Isoprop | H2O |
|---|---|---|---|---|---|---|---|---|---|---|
| *C. elegans* miR-39 | 23.31 | 22.90 | 23.27 | 23.85 | 22.97 | 23.36 | 23.09 | 23.42 | 23.18 | 22.62 |
| miR-16 | 22.96 | 22.78 | 23.09 | 23.23 | 22.40 | 22.31 | 22.04 | 24.31 | 24.22 | 24.50 |
| miR-21 | 25.56 | 25.84 | 25.80 | 25.84 | 25.04 | 24.74 | 24.63 | 25.98 | 26.73 | 26.57 |
| miR-191 | 26.95 | 27.26 | 26.88 | 27.50 | 26.00 | 26.23 | 25.95 | 31.15 | 29.59 | 29.97 |
| miRTC | 21.53 | 21.53 | 21.65 | 21.54 | 21.75 | 21.48 | 21.67 | 21.65 | 21.61 | 21.51 |
| PPC | 19.39 | 19.28 | 19.47 | 19.40 | 19.35 | 19.31 | 19.40 | 19.42 | 19.54 | 19.39 |

| | STD | | | | | | | | | |
|---|---|---|---|---|---|---|---|---|---|---|
| | Acetone | Acetonitrile | Dioxane | DMF | DMSO | NMP | THF | EtOH | Isoprop | H2O |
| *C. elegans* miR-39 | 0.688 | 0.257 | 0.501 | 1.023 | 0.140 | 0.251 | 0.180 | 0.208 | 0.112 | 0.215 |

-continued

| | \multicolumn{10}{c}{STD} |
| | Acetone | Acetonitrile | Dioxane | DMF | DMSO | NMP | THF | EtOH | Isoprop | H2O |
|---|---|---|---|---|---|---|---|---|---|---|
| miR-16 | 0.313 | 0.100 | 0.918 | 1.190 | 0.064 | 0.025 | 0.130 | 0.150 | 0.412 | 0.139 |
| miR-21 | 0.242 | 0.070 | 1.015 | 1.079 | 0.022 | 0.059 | 0.260 | 0.079 | 0.331 | 0.146 |
| miR-191 | 0.337 | 0.045 | 0.983 | 1.104 | 0.068 | 0.066 | 0.195 | 0.313 | 0.031 | 0.182 |
| miRTC | 0.088 | 0.083 | 0.189 | 0.112 | 0.024 | 0.129 | 0.074 | 0.017 | 0.030 | 0.134 |
| PPC | 0.066 | 0.091 | 0.035 | 0.254 | 0.161 | 0.191 | 0.076 | 0.024 | 0.059 | 0.074 |

Figure 10:
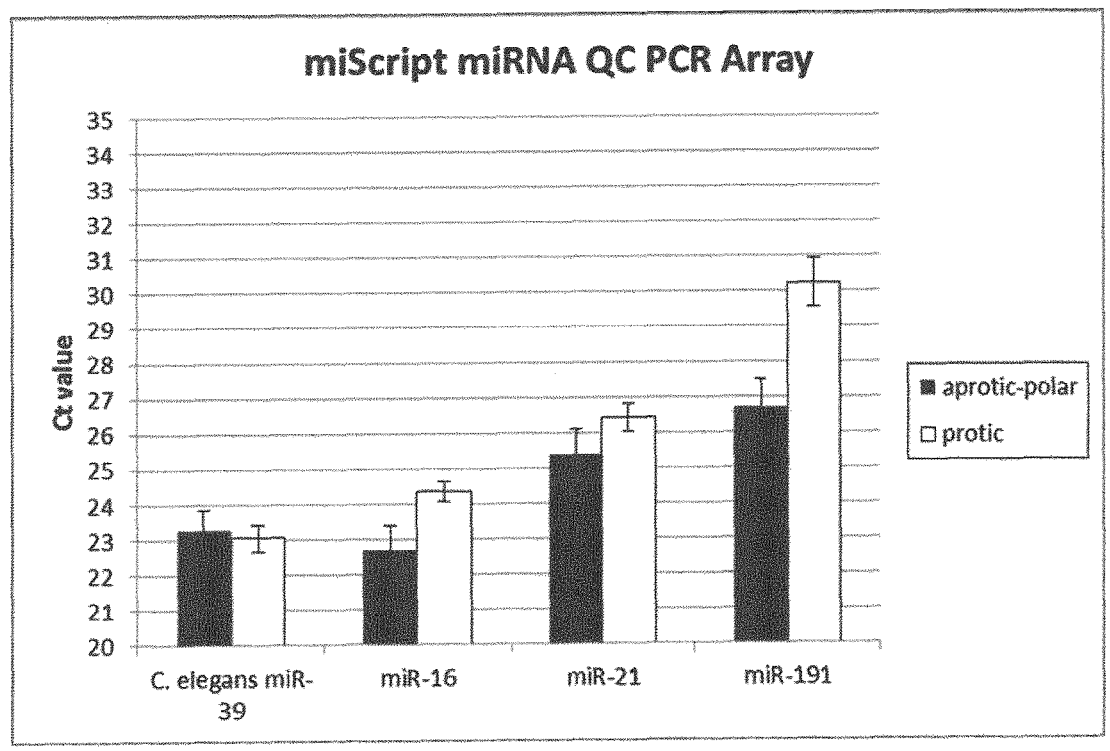
FIG. 10: shows the qRT-PCR results of the miScript miRNA QC PCR Array. The eluates of different miRNA preparations from serum using different organic solvents in the precipitation buffer were analyzed. Shown are the mean values of all results that were obtained using either an aprotic polar organic solvent or a protic solvent.

As is evident from the above results and FIG. 10, example 6 confirms the observation described above, that the isolation of small RNAs is not negatively influenced by the presence of an organic solvent as claimed. Small RNA is successfully recovered with good yield. Furthermore, the miRNA yield was even improved when using an aprotic polar organic solvent.

However, for isolating large RNA in addition to small RNA, it is mandatory that an organic solvent as claimed is present during the protein precipitation step in order to prevent that these large RNAs get lost during the protein precipitation step thereby ensuring that they can be recovered in the subsequent RNA isolation step from the protein-depleted supernatant. Furthermore, as the results show, using an aprotic polar organic solvent provides better results, in particular with respect to the isolation of larger RNAs and also high molecular weight DNA.

Example 7: The Buffering Agent and the pH Value

Figure 11:
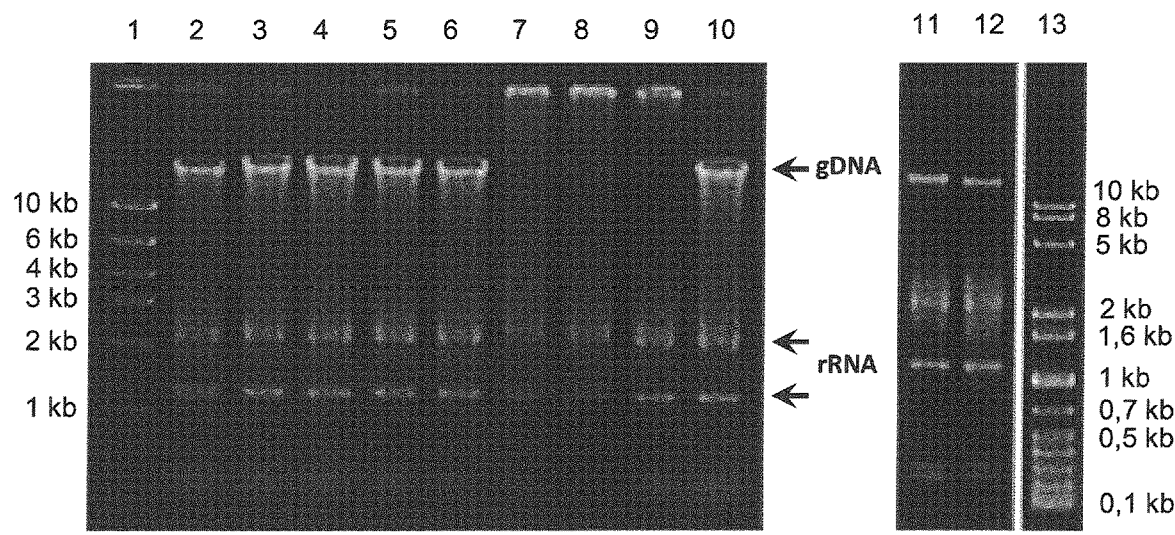
FIG. 11: Shown is a gelelectrophoretic separation of the nucleic acid containing eluates, which were obtained using the precipitation method according to the present invention wherein different sodium acetate substitutes were tested in the precipitation buffer. The nucleic acids were isolated from cell lysates. 1.5 µl of each eluate was separated for an hour in a non-denaturing agarose gel (0.8%) with constant 120 V. As sodium acetate substitutes the following buffering agents were tested in the same concentration and at the same pH value: Sodium citrate, magnesium acetate, ammonium acetate and potassium acetate. Furthermore, RNA was isolated i) without sodium acetate ($H_2O$), ii) with a protocol wherein sodium acetate was added after precipitation ($H_2O$+NaOAc) and iii) with a protocol wherein sodium chloride (NaCl) was used instead of sodium acetate. Additionally, RNA was isolated using 0.4 M PIPPS (pH 4.3) in the precipitation buffer as buffering agent substitute for the acetate buffer.

The precipitation buffer XP comprises sodium acetate. Sodium acetate may serve two important functions. First, the acetate compound can provide a pH buffering effect. Furthermore, the monovalent sodium ions could support the neutralization of the charge of the nucleic acids and therefore could support the binding of the nucleic acids to the solid phase. The second effect is not relevant for the actual protein precipitation step. Therefore, it was tested whether the sodium acetate can be exchanged by other acetates, in particular by divalent magnesium acetate. The results demonstrate that omission of the acetate and hence the buffering agent from the precipitation buffer led to significant differences in the spectrum of nucleic acids that were isolated. Furthermore, also the subsequent addition of sodium acetate after completion of the precipitation step could not restore the original spectrum. This supports the conclusion, that the primary effect of the sodium acetate is the buffering of the pH value and that this buffering is advantageous in order to provide good RNA isolation results. This is further confirmed by additional experiments, wherein it was shown that instead of sodium acetate also other buffering agents could be used as alternative, such as a citrate buffer or piperazine-1,4-bis(propane sulfonic acid) buffer (PIPPS). These alternative buffering agents likewise allowed the isolation of high molecular nucleic acids as is shown in FIG. 11.

Figure 12:
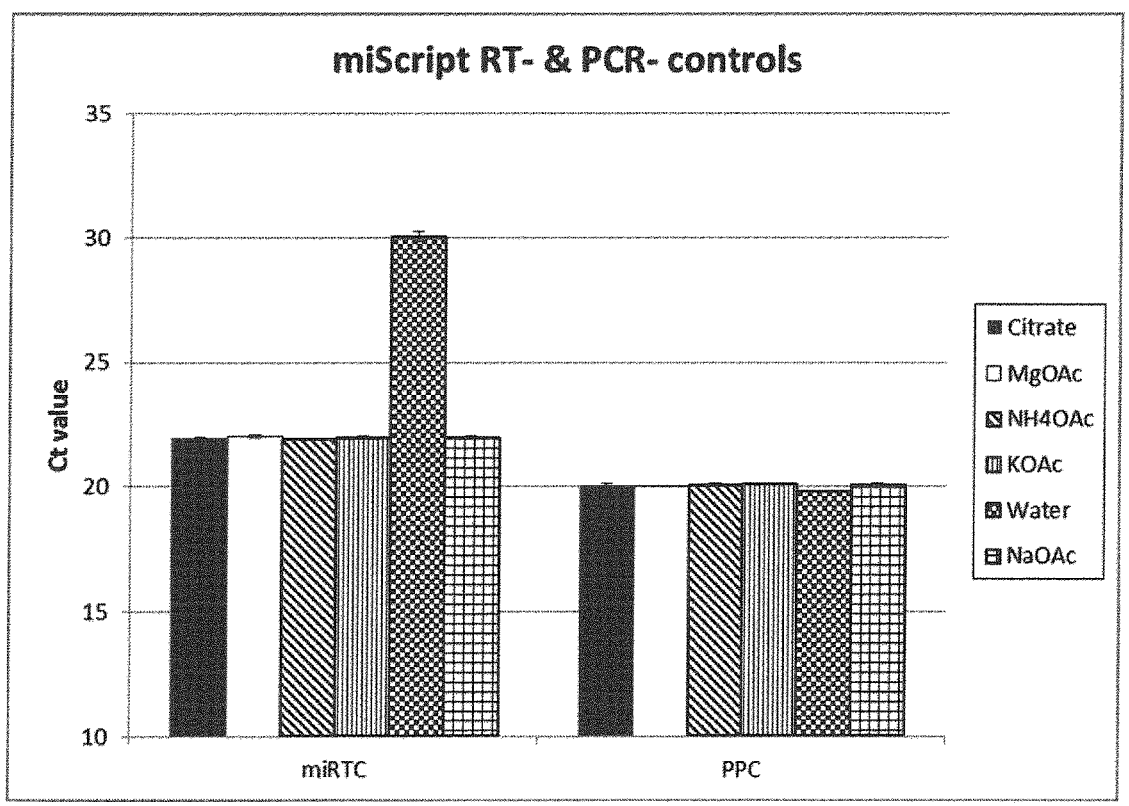
FIG. 12: Shows the qRT-PCR results of the controls of the miScript miRNA QC PCR Array. The eluates obtained from different RNA isolations from serum using different sodium acetate substitutes in the precipitation buffer were analyzed.

The samples that were prepared without a pH buffering agent showed after the protein precipitation step a higher pH value (pH 5.5) as those prepared with a buffering agent containing precipitation buffer (pH 4.3). Furthermore, when isolating RNA from serum samples instead of cell lysates, the sample was turbid after addition of isopropanol during the RNA binding step. Therefore, it was found that buffering the pH value of the precipitation mixture and hence during the precipitation step is advantageous, in order to prevent a contamination and/or clogging of the solid phase, which in particular applies if complex samples such as serum are processed and if a column is used. Furthermore, samples that were prepared with a precipitation solution not containing a buffering agent (see "water") showed significantly more inhibition of the reverse transcription reaction in the subsequently performed miScript miRNA analysis. The results are shown in FIG. 12 (miRTC=Reverse Transcription Control; PPC=Positive PCR Control).

Figure 13:
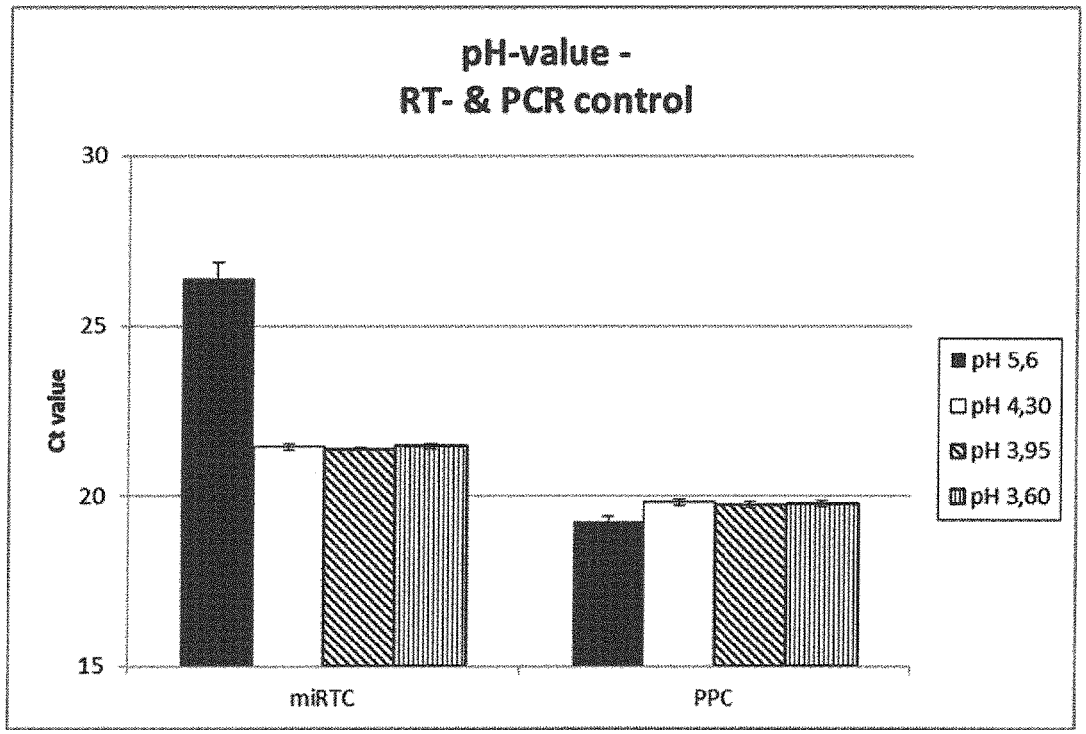
FIG. 13: Shows the qRT-PCR results of the controls of the miScript miRNA QC PCR Array. The eluates of different RNA isolation protocols from serum using different pH-buffered precipitation buffers were analyzed.

Additionally, analysis of the miRNA prepared using different pH values in the XP precipitation buffer confirmed the above observations. When processing protein rich complex samples (here: serum samples), lower pH values of the precipitation buffer prevented precipitations after the addition of alcohol in the RNA binding step and thereby supported the prevention of contaminations or clogging of the used column. The results are shown in FIG. 13.

Furthermore, different concentrations of the buffering agent were tested. The results confirm that the buffering agent can be used over a broad concentration range. The standard precipitation buffer XP was used (see above), wherein, however, the concentration of sodium acetate was varied. The following concentrations of sodium acetate in the precipitation buffer XP were tested: 227 mM, 455 mM, 682 mM, 909 mM, 1136 mM and 1591 mM (corresponding to 52 mM, 104 mM, 156 mM, 208 mM, 260 mM and 364 mM sodium acetate in the precipitation mixture). The following two tables show the results for the detection of different miRNAs obtained from two replicates and the standard deviation (std):

| | 52 mM | 104 mM | 156 mM | 208 mM | 260 mM | 364 mM |
|---|---|---|---|---|---|---|
| C. elegans miR-39 | 25.43 | 24.10 | 23.89 | 23.96 | 24.29 | 25.57 |
| miR-16 | 29.28 | 23.11 | 23.07 | 23.38 | 23.69 | 24.75 |
| miR-21 | 30.42 | 25.98 | 25.50 | 25.95 | 26.14 | 27.18 |
| miR-191 | 32.40 | 27.82 | 27.49 | 27.37 | 28.09 | 29.22 |
| miRTC | 26.18 | 21.78 | 21.72 | 21.64 | 21.55 | 21.32 |
| PPC | 19.41 | 19.35 | 19.30 | 19.36 | 19.29 | 19.29 |

| | \multicolumn{6}{c}{STD} |
| | 52 mM | 104 mM | 156 mM | 208 mM | 260 mM | 364 mM |
|---|---|---|---|---|---|---|
| C. elegans miR-39 | 0.694 | 0.298 | 0.181 | 0.527 | 0.501 | 0.635 |
| miR-16 | 3.009 | 0.409 | 0.512 | 0.507 | 0.314 | 0.034 |
| miR-21 | 4.026 | 0.493 | 0.246 | 0.472 | 0.326 | 0.109 |
| miR-191 | 0.808 | 0.384 | 0.810 | 0.522 | 0.169 | 0.647 |
| miRTC | 2.094 | 0.091 | 0.050 | 0.060 | 0.201 | 0.139 |
| PPC | 0.107 | 0.099 | 0.080 | 0.089 | 0.126 | 0.041 |

Particularly preferred is a concentration of 125 mM to 300 mM or 150 mm to 275 mM in the precipitation mixture.

Example 8: The Metal Cations Used in the Precipitation Buffer

As described above, in the precipitation buffer, zinc serves the function to precipitate proteins. In an artificial set-up using BSA (40 g/l) in PBS as serum substitute, proteins could likewise be precipitated using trivalent aluminum ions instead of zinc. Divalent calcium or mangane ions also precipitated the proteins, however, only slowly under the tested conditions (pH value, concentration, solvent) and therefore, are less suitable than $Zn^{2+}$ and $Al^{3+}$. Therefore, according to one embodiment, such slow metal cation precipitants are not used. Zinc is preferred.

Figure 14:
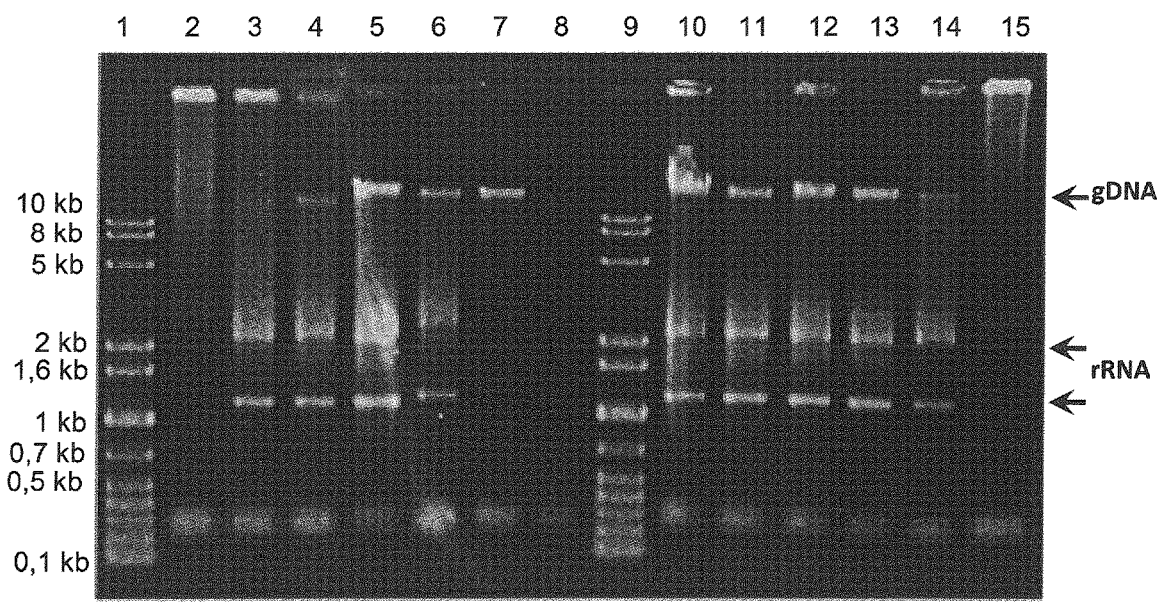
FIG. 14: Shows a gel electrophoretic separation of nucleic acid containing eluates that were obtained with the precipitation based protocol using a precipitation buffer which comprised different concentrations of DMSO and zinc chloride. RNA was isolated from cell lysates. 1.5 µl of the eluates were separated for 1 hour in a non-denaturing agarose gel (0.8%) at constant 120 V.
Figure 15:
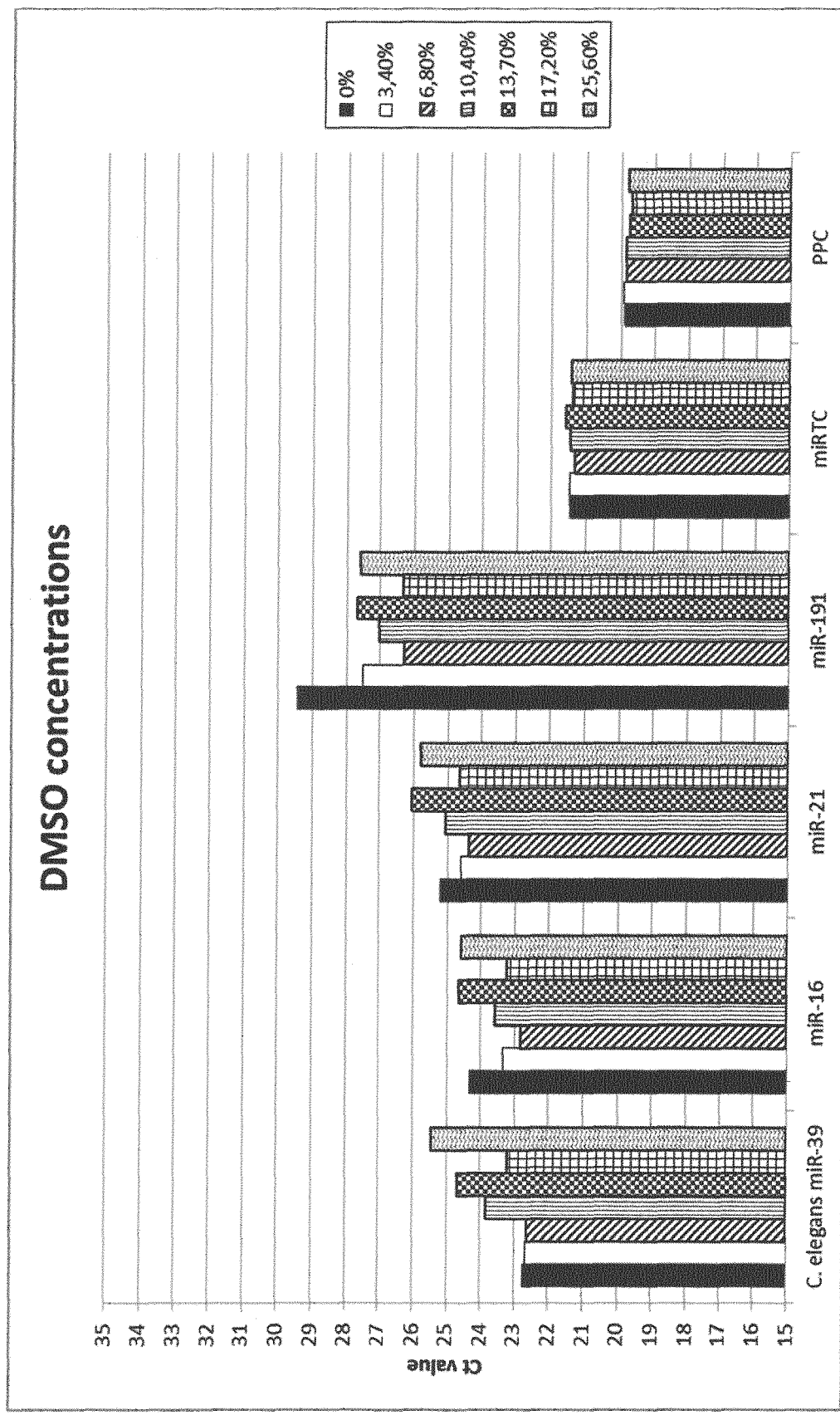
FIGS. 15 and 16: Shows the qRT-PCR results of the miScript miRNA QC PCR Array. The same volume of eluates were analyzed. The eluates were obtained from different RNA isolation protocols from serum using precipitation buffers with different DMSO and zinc concentrations. Indicated is the final concentration of these components in the precipitation mixture and hence when precipitation occurs.

Example 9: Concentration Ranges for the Organic Solvent and the Metal Cation Precipitant Additionally, different concentrations of the organic solvent and the metal cation (zinc) were analyzed. Nucleic acids were isolated from cell lysates and serum samples. FIG. 14 shows the concentration of the respective components in the precipitation mixture (comprising the sample, lysis buffer and the precipitation buffer XP).

Results for the Concentration of the Organic Solvent

As is demonstrated by FIG. 14, already 15% DMSO in the precipitation buffer (final concentration in the precipitation mixture 3.4%) is suitable in order to also efficiently isolate large RNAs. When using 30% DMSO in the precipitation buffer XP (final concentration in the precipitation mixture 6.9%) additionally, high molecular nucleic acids such as genomic DNA could be isolated. Therefore, the choice of the concentration of the organic solvent influences which type of nucleic acid remains present in the supernatant and hence, can be isolated. Using higher concentrations of 75% DMSO in the precipitation buffer (final concentration in the precipitation mixture 17.2%), however, reduced the yield of large RNAs while high molecular DNA could still be isolated from the supernatant. Even higher concentrations of DMSO resulted in that only small RNA could be isolated. However, here, also the overall yield of small RNA appeared to be reduced according to the gel analysis (see FIG. 14, 25.6% DMSO). Therefore, the concentration of the organic solvent that is used according to the present invention in the precipitation mixture is important and the preferred concentration range lies between 3.4-15% in the precipitation mixture. These concentrations can be achieved for example using a precipitation buffer comprising between 15% and 60% of the organic solvent according to the invention. The respective concentration ranges are particular suitable to provide after removal of the precipitate a protein-depleted supernatant that comprises small as well as large RNA which can then be isolated from said supernatant. Analysis of the isolated miRNA showed that small nucleic acid was isolated similarly well whether DMSO was present or absent as long as the concentration was not too high. For several miRNAs the results were even improved if the organic solvent is present as is e.g. demonstrated by FIGS. 4 and 14. E.g. miR-191 can be isolated more efficiently, if DMSO is present (at least 3.4% final concentration in the precipitation mixture). To enable the isolation of large RNA, the organic solvent is very important as is demonstrated herein. If no organic solvent is present or if the concentration is too high and thus lies outside the claimed range, large RNA is not present respectively is present in only low amounts in the supernatant.

Results for the Precipitation Agent Zinc Chloride

Figure 16:
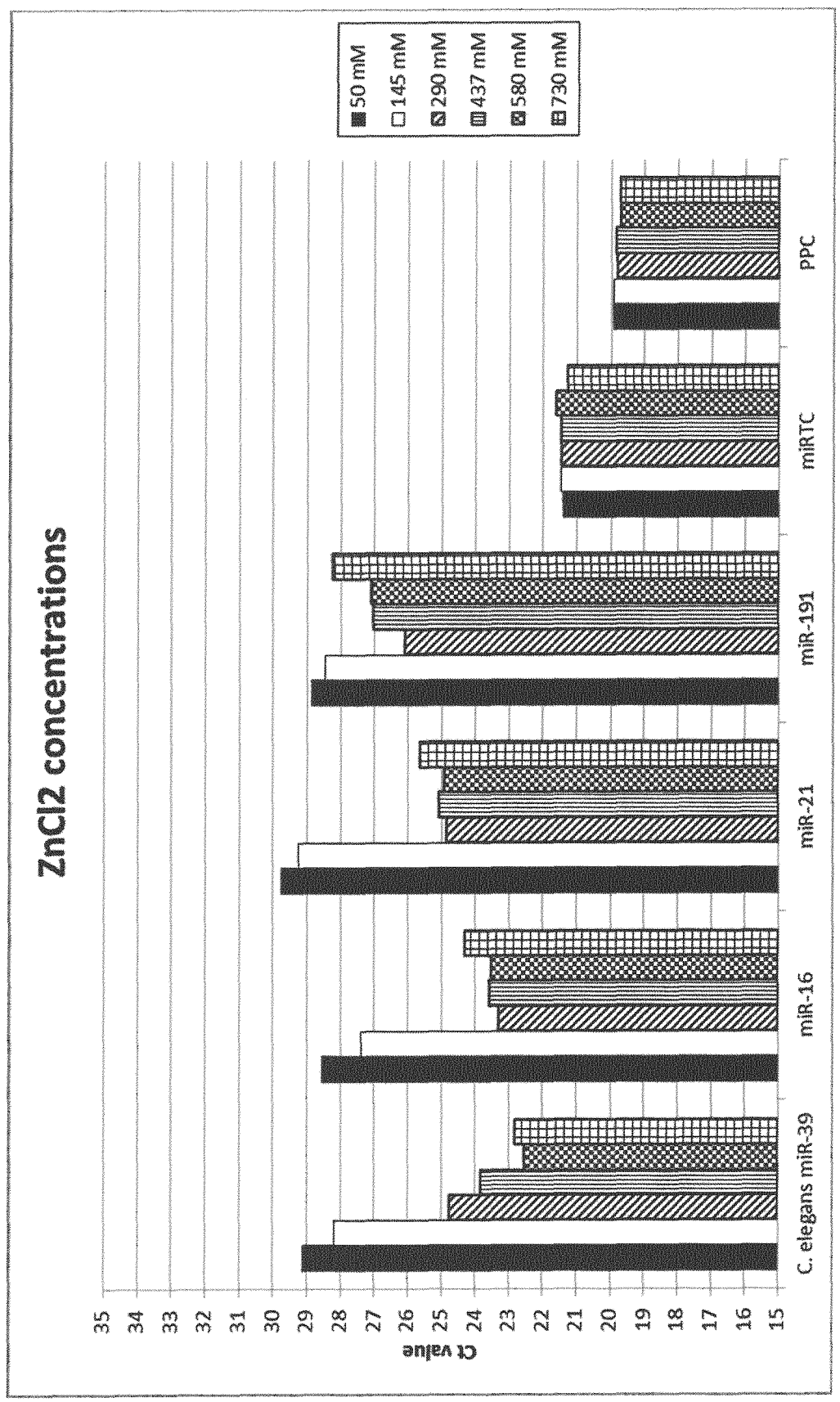

The results are shown in FIG. 14 and FIG. 16. In case of the precipitation agent zinc chloride, already the smallest tested amount of zinc chloride (0.212 M in the precipitation buffer, which corresponds to 48 mM final concentration in the precipitation mixture) is sufficient in order to precipitate proteins. Zinc chloride concentrations up to 2.55 M in the precipitation buffer (final concentration in the precipitation mixture 582 mM) are likewise suitable to provide total nucleic acid preparations from cell lysates. When using much higher concentrations (3.18 M in the precipitation buffer XP, what corresponds to 728 mM final concentration in the precipitation mixture) the isolation of high molecular acids is disturbed as is evident from FIG. 14. With respect to the miRNA isolation from serum it was shown that the concentration of 0.212 M and 0.63 M zinc chloride in the precipitation buffer (final concentration 48 mM respectively 145 mM) does not contribute as efficiently to the isolation of miRNA, as the tested higher concentrations. Therefore, a preferred range for the metal cation precipitant is e.g. 290 to 580 mM in the precipitation mixture. This can be achieved by using a precipitation buffer comprising for example 1.27 to 2.55 M zinc chloride.

Example 10: Addition of the Disruption Reagent

In example 10 it was tested whether it is critical for complex samples such as serum samples that the sample is disrupted prior to preparing the precipitation mixture and hence prior to adding the precipitation buffer. As reference, the standard procedure described above was followed. First, 120 µl disruption reagent (lysis buffer RLT Plus) is added to the serum sample, incubated and then 95 µl XP buffer is added. In a variation of this standard method 95 µl XP-buffer was mixed with 120 µl RLT Plus and the respective mixture was then added to the serum sample. Therefore, in this embodiment, preparation of the precipitation mixture and disruption of the sample occurred at the same time. The results are shown in the subsequent tables:

|  | Reference | XP (95) + RLT Plus |
| --- | --- | --- |
| C. elegans miR-39 | 24.27 | 23.83 |
| miR-16 | 24.90 | 24.20 |
| miR-21 | 27.74 | 27.24 |
| miR-191 | 28.99 | 29.91 |
| miRTC | 21.94 | 21.91 |
| PPC | 20.62 | 20.63 |

| | STD | |
| --- | --- | --- |
|  | Reference | XP (95) + RLT Plus |
| C. elegans miR-39 | 0.284 | 0.230 |
| miR-16 | 0.539 | 0.037 |
| miR-21 | 0.567 | 0.096 |
| miR-191 | 0.250 | 0.356 |
| miRTC | 0.119 | 0.060 |
| PPC | 0.110 | 0.165 |

As can be seen, it essentially did not make a difference whether the lysis buffer was added prior to or during preparation of the precipitation mixture. Therefore, it is not mandatory to first disrupt the sample before the precipitation buffer is added. However, it was found that it is beneficial, that a disruption agent, preferably a chaotropic salt, is present during the precipitation process.

Example 11: Precipitation of Samples Lysed with Disrupting Reagent

To also test precipitation in the presence of different higher chaotropic agent concentrations, a batch lysate was prepared from rat liver tissue by lysing 800 mg tissue in 5 ml lysis buffer comprising 5.8 M GTC, 30 mM sodium citrate, pH 5.0 in the presence of 1% beta-mercaptoethanol. The lysate was homogenized and filtered through a QIAshredder in order to remove remaining solid particles. To vary the concentration of chaotropic salt (GTC) during precipitation, the lysate obtained was then diluted with different amounts of dilution buffer (30 mM sodium citrate, pH 5.0) having the same composition as the lysis buffer but lacking the chaotrope, and with lysis buffer. The amounts of lysate, dilution buffer and lysis buffer used are shown in the below table. The table also shows the chaotropic agent concentration in the obtained diluted lysate and the final chaotropic salt concentration present in the precipitation mixture.

| | | | | |
|---|---|---|---|---|
| Volume batch lysate (µl) | 67.2 | 67.2 | 67.2 | 67.2 |
| Volume dilution buffer (µl) | 31.0 | 64.7 | 98.3 | 131.9 |
| Volume lysis buffer (µl) | 201.7 | 168.1 | 134.5 | 100.9 |
| GTC concentration in dilution (M) | 5.20 | 4.55 | 3.90 | 3.25 |
| GTC concentration in precipitation mixture (M) | 4.0 | 3.5 | 3.0 | 2.5 |

Figure 17:
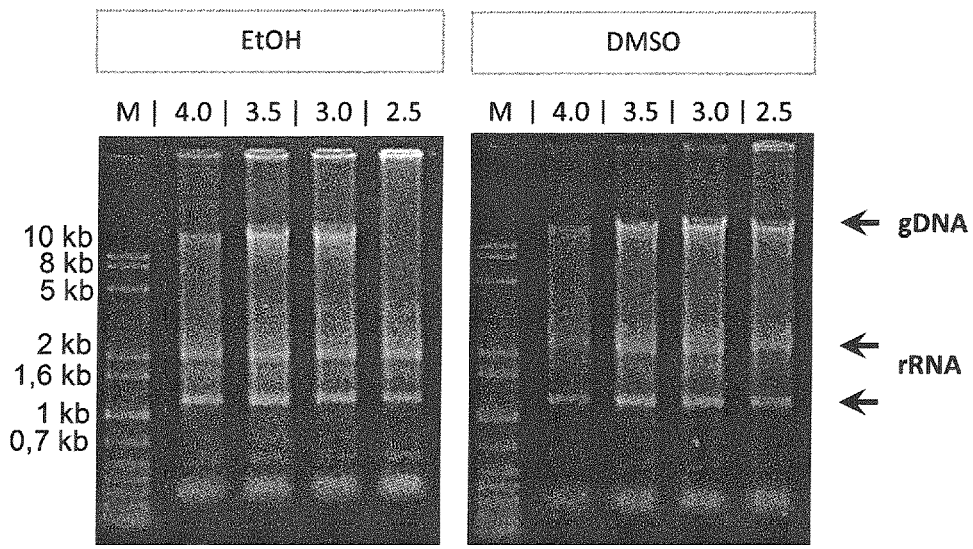
FIG. 17: Shows a gel electrophoretic separation of nucleic acid containing eluates that were obtained with the precipitation based protocol from disrupted samples comprising different chaotropic agent concentrations, using EtOH or DMSO as organic solvents. M=Marker; chaotropic agent concentrations (M) in the precipitation mixture are indicated for each lane.

The diluted lysates (300 µl) were then mixed with precipitation buffer XP or with a precipitation buffer having the same composition but comprising the protic solvent ethanol instead of DMSO. After the precipitation, the sample was centrifuged and nucleic acids were isolated from the obtained supernatant. To that end, the supernatant was mixed with an equal volume (340 µl) of isopropanol. The mixture was applied on an RNeasy column. After the nucleic acid was bound, the column was washed with 700 µl buffer RW1, followed by two washes with 700 µl RPE and elution with 50 µl H$_2$O. Subsequently, the nucleic acids were separated on a gel.
Results
FIG. 17 shows the results obtained. Protic (EtOH, left gel) and aprotic (DMSO, right gel) organic solvents were used. M=Marker; chaotropic salt concentrations in the precipitation mixture (ranging from 4.0 to 2.5 M) are indicated for each lane. The results demonstrate that large nucleic acids including large RNA can be isolated over a range of chaotropic agent concentrations and in the presence of protic and aprotic organic solvents. The exemplary range of 4.0 to 2.5 M tested yielded good results.

Example 12: Concentration Ranges of Aprotic and Protic Organic Solvents

Figure 18:
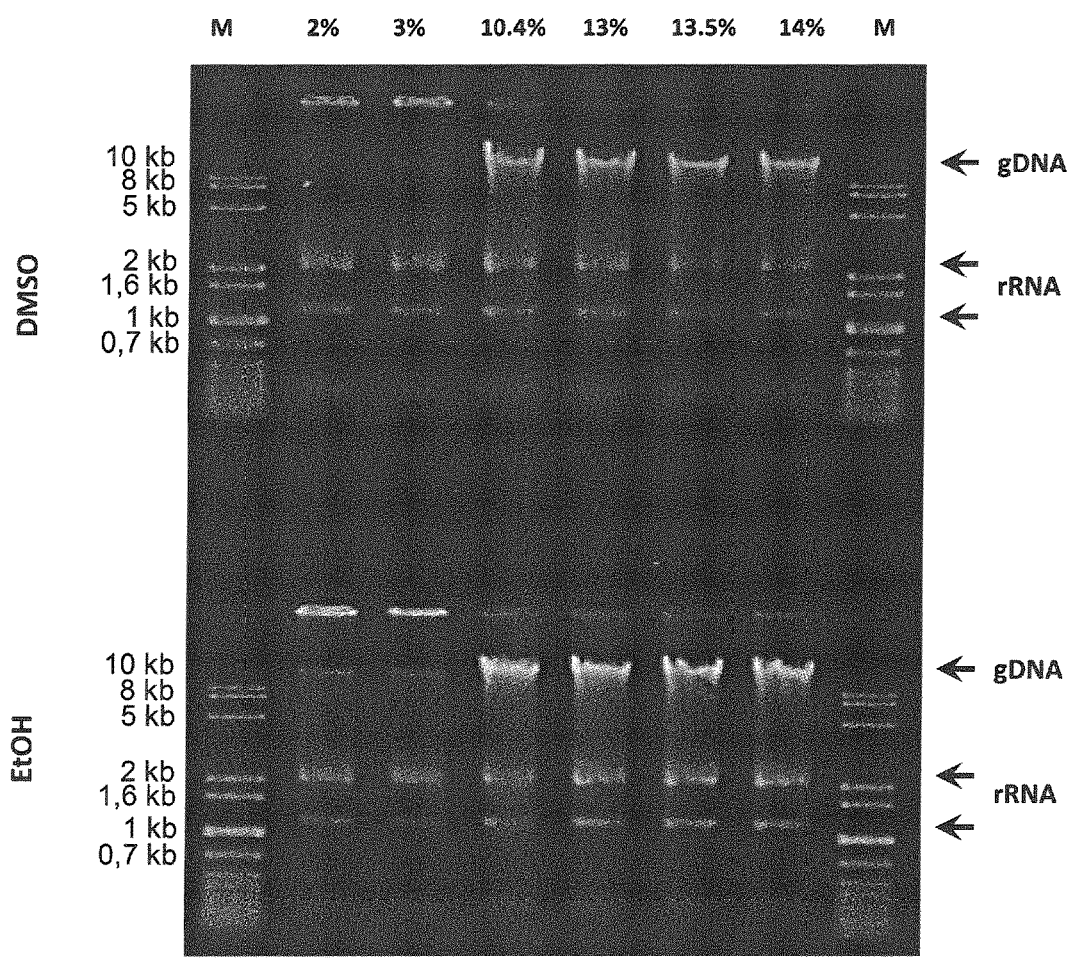
FIG. 18: Shows a gel electrophoretic separation of nucleic acid containing eluates that were obtained with the precipitation based protocol, using a precipitation buffer which comprised different concentrations of DMSO or EtOH. M=Marker; percent values for each lane indicate the percent DMSO or EtOH in the precipitation mixture.

Additionally, further concentrations of the organic solvent were analyzed. DMSO and EtOH were used as exemplary aprotic and protic solvents, respectively. Nucleic acids were isolated and a gel was run to separate nucleic acids contained in eluates that were obtained with the precipitation based protocol using a precipitation buffer which comprised different concentrations of DMSO or EtOH.
Results
The results are shown in FIG. 18. The figure shows the results for DMSO (upper panel) and EtOH (lower panel). M=Marker; percent values for each lane indicate the percent DMSO or EtOH in the precipitation mixture. As is demonstrated by FIG. 18, a final concentration of 2% aprotic or protic organic solvent in the precipitation mixture is already suitable in order to efficiently isolate large RNAs. This finding was also confirmed using a slightly higher concentration of 3% DMSO or EtOH. High molecular nucleic acids such as genomic DNA could also be isolated at the further tested concentrations, thereby confirming the finding of Example 9 that genomic DNA could be isolated at a final organic solvent concentration of 6.9%. Large RNAs could still be recovered from the eluates also when comparably high organic solvent concentrations of 14% were used.

Therefore, concentrations of aprotic or protic organic solvent as low as 2% are suitable to provide after removal of the precipitate a protein-depleted supernatant that still comprises large nucleic acids including large RNA in addition to small RNA. Small and large nucleic acids therefore can be isolated from said supernatant. The present example confirms that large RNA can be isolated also at higher concentrations of organic solvent within the range defined herein, such as e.g. 14%, as long as the concentration is not too high (see Example 9 above). Moreover, the example confirms the suitability of protic and aprotic organic solvents for stabilizing large nucleic acids during protein precipitation.

Example 13: Isolation of Large Nucleic Acids Using Precipitation Buffers of Different Acidic pH-Values A batch lysate was prepared from rat liver tissue by lysing 400 mg tissue in 6 ml lysis buffer comprising 2.78 M GTC, 20 mM sodium citrate, pH 5.0 in the presence of 1% beta-mercaptoethanol. The lysate was homogenized and filtered through a QIAshredder in order to remove remaining solid particles. XP-buffers with different pH values were prepared by adjusting the pH with acetic acid.

For each pH-value to be tested, 300 µl of the lysate were combined with 90 µl of the respective XP-buffer. The precipitate was removed by centrifugation, and the clear supernatant (approx. 360 µl) was combined with 440 µl of isopropanol to yield a final isopropanol concentration of 55%. The mixture was applied to an RNeasy column. After centrifugation, the column was washed once with 700 µl of buffer RW1, followed by two washes with 700 µl RPE and elution with 50 µl H$_2$O. The concentration and purity of the isolated nucleic acid was determined.
Results
Results for the different tested pH values 3.30 to 4.75 are shown in the below table:

| | Conc. [ng/µl] | 260/280 | 260/230 |
|---|---|---|---|
| pH 4.75 | 1197.0 | 1.97 | 2.12 |
| pH 4.50 | 1143.0 | 1.93 | 2.17 |
| pH 4.30 | 1198.5 | 2.01 | 1.82 |
| pH 3.30 | 1296.5 | 2.00 | 2.14 |

These results again demonstrate that large RNA can be isolated in good yield from the supernatant after protein precipitation using precipitating buffers of different acidic pH-values.

Example 14: Isolation of Small RNA Using Precipitation Buffers of Different pH-Values In a further experiment, RNA was isolated from serum samples using precipitation buffer XP as described in the standard protocol. The pH-value of the precipitation buffer was adjusted with acetic acid to yield buffers of different acidic pH-values.

Results

Figure 19:
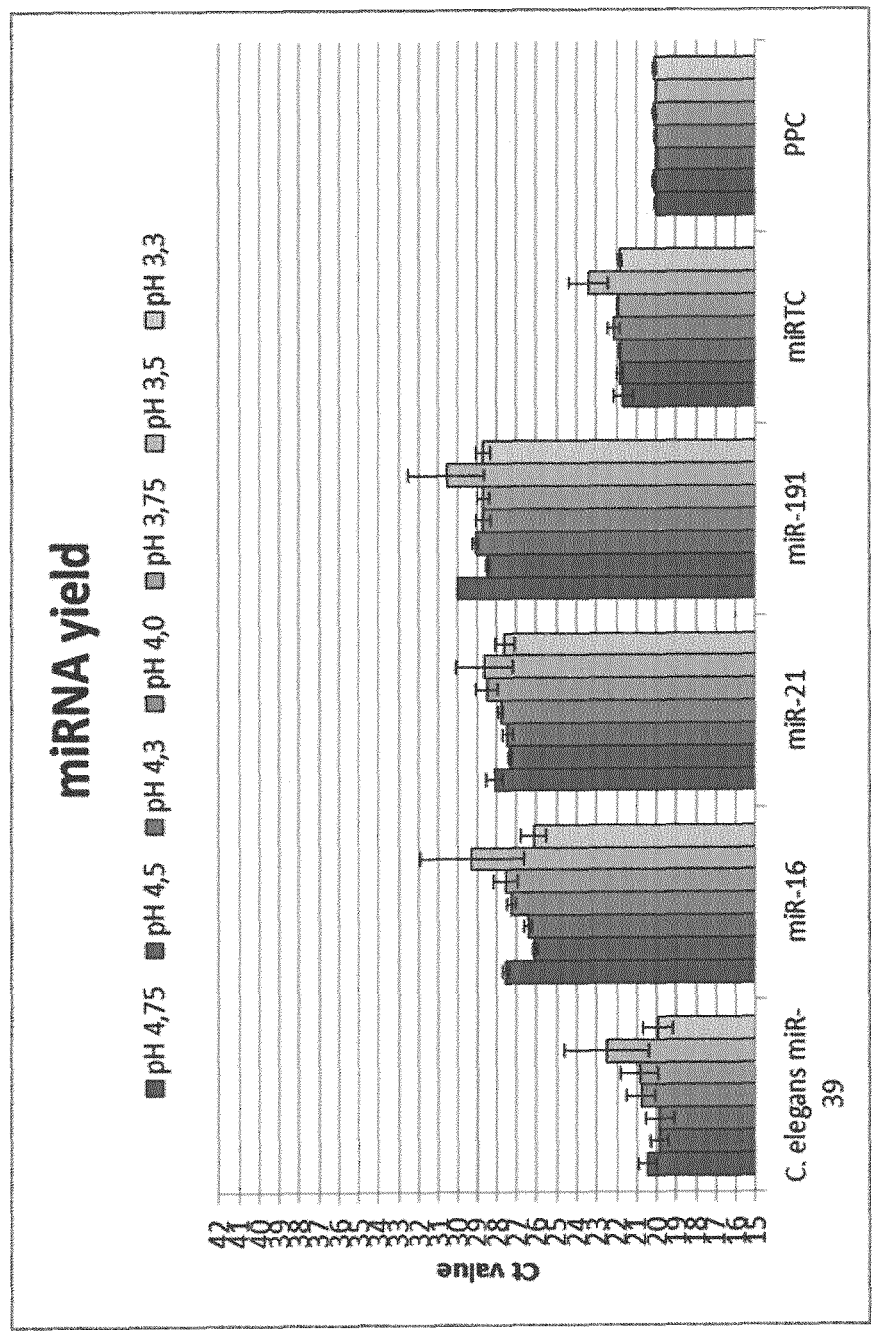
FIG. 19: Shows qRT-PCR results of the controls of the miScript miRNA QC PCR Array. The eluates of different RNA isolations from serum using precipitation buffers of different pH-values were analyzed. miRNAs were isolated with good yield; miRTC=Reverse Transcription Control; PPC=Positive PCR Control.

The results of example 7 were confirmed for additional pH-values. With pH-values ranging from pH 3.3 to pH 4.75, it was possible to avoid turbidity after addition of isopropanol during the RNA binding step also in complex, protein rich serum samples. Contamination and clogging of the column were avoided. miRNAs were isolated with good yield; results of miRNA analysis using the miScript assay are shown in FIG. 19 (miRTC=Reverse Transcription Control; PPC=Positive PCR Control).

The invention claimed is:

1. A phenol-free method for isolating a nucleic acid from a sample, said method comprising the following steps:
   a) preparing a precipitation mixture by adding at least one metal cation precipitant and at least one organic solvent selected from aprotic polar solvents and protic solvents to the sample, wherein the precipitation mixture
      i) comprises the metal cation precipitant;
      ii) comprises the organic solvent in a concentration of 15% or less;
      iii) comprises at least one buffering agent; and
      iv) has an acidic pH value,
      and precipitating proteins in the sample;
   b) separating the precipitate from the supernatant, wherein the supernatant comprises small RNA having a length of less than 200 nt and large RNA having a length of at least 1000 nt; and
   c) isolating a nucleic acid from the supernatant.

2. The method according to claim 1, wherein the precipitation mixture comprises the organic solvent in a concentration of 2% to 15% and wherein the organic solvent is water-miscible.

3. The method according to claim 1, wherein the nucleic acid to be isolated is RNA and wherein step c) comprises isolating at least small and/or large RNA from the supernatant.

4. The method according to claim 3, wherein step c) comprises:
   aa) adding at least one alcohol to the supernatant to provide a binding mixture which comprises the alcohol in a concentration ≥35% or ≥40%;
   bb) binding total RNA contained in the binding mixture to a silicon containing nucleic acid binding solid phase, wherein after step bb), at least large and small is bound to the solid phase;
   cc) optionally washing the bound RNA; and
   dd) eluting RNA from the solid phase.

5. The method according to claim 1, having one or more of the following characteristics:
   i) the metal cation precipitant is $Zn^{2+}$ or $Al^{3+}$; and/or
   ii) the metal cation precipitant is added in form of a solution and wherein the precipitation mixture provided in step a) comprises the metal cation precipitant in a concentration selected from 200 mM to 675 mM, 250 mM to 650 mM, 300 mM to 625 mM, 350 mM to 600 mM or 400 mM to 550 mM; and/or
   iii) the metal cation precipitant is added in the form of a solution which comprises a dissolved salt of the metal cation precipitant.

6. The method according to claim 1, having one or more of the following characteristics:
   i) the precipitation mixture provided in step a) comprises the organic solvent in a concentration selected from 3% to 15%, 5% to 14.5%, 6% to 14%, 7% to 13.5%, 8% to 13%, 9% to 12.5% or 9.5% to 12%;
   ii) the organic solvent is an aprotic polar solvent;
   iii) the organic solvent is an aprotic polar solvent that is selected from the group consisting of dimethylsulfoxide (DMSO), acetone, acetonitrile, tetrahydrofurane (THF), dioxane, 1-methyl-2-pyrolidone (NMP) and dimethyl-formamide (DMF);
   iv) the organic solvent is a protic solvent which is an alcohol;
   v) the organic solvent is a protic solvent which is a water-miscible alcohol, and/or
   vi) the organic solvent is a protic solvent which is a water-miscible alcohol which is selected from the group consisting of ethanol and isopropanol.

7. The method according to claim 1, wherein the pH value during precipitation is <5.5, <5.25, <5, <4.75, <4.5 or <4.4.

8. The method according to claim 1, wherein step a) comprises adding a precipitation buffer to the sample, wherein said precipitation buffer comprises the metal cation precipitant, the organic solvent and the buffering agent.

9. The method according to claim 8, wherein the precipitation buffer has one or more of the following characteristics:
   i) it comprises the metal cation precipitant in a concentration selected from 0.75M to 3 M, 1 M to 2.8M, 1.25M to 2.7M, 1.5M to 2.6M or 1.7M to 2.5M;
   ii) it comprises the organic solvent in a concentration selected from 13% to 65%, 20% to 63%, 25% to 62.5%, 30% to 60%, 33% to 57.5%, 37.5% to 55% or 40% to 52.5%; and/or
   iii) it has a pH value selected from 3 to 5, 3.25 to 4.75, 3.5 to 4.5 or 3.75 to 4.4.

10. The method according to claim 1, wherein the nucleic acid to be isolated is RNA and wherein in step c), RNA is isolated using a nucleic acid binding solid phase and wherein at least one alcohol and/or at least one chaotropic salt is used to establish RNA binding conditions.

11. The method according to claim 10, wherein step c) comprises adding at least one alcohol to the supernatant to establish the RNA binding conditions and wherein the alcohol that is added in step c) has one or more of the following characteristics:
   i) it is a branched or unbranched aliphatic alcohol with 1 to 5 carbon atoms;
   ii) it is selected from methanol, ethanol, propanol, isopropanol and butanol and mixtures thereof;
   iii) it is selected from isopropanol and ethanol; and/or
   iv) it is isopropanol.

12. The method according to claim 1, wherein the sample is disrupted and wherein sample disruption occurs prior to addition of the metal cation precipitant and the organic solvent and/or at the same time/stage when the precipitation mixture is prepared.

13. The method according to claim 12, wherein the method comprises
   x) disrupting the sample;
   a) preparing a precipitation mixture by adding at least one metal cation precipitant and at least one organic solvent selected from aprotic polar solvent and protic solvents to the disrupted sample to prepare a precipitation mixture which
      i) comprises the metal cation precipitant;
      ii) comprises the organic solvent in a concentration of 15% or less;

iii) comprises a buffering agent; and
iv) has an acidic pH value,
and precipitating proteins in the sample;
b) separating the precipitate from the supernatant, wherein the supernatant comprises small RNA having a length of less than 200 nt and large RNA having a length of at least 1000 nt; and
c) isolating a nucleic acid from the supernatant;
or wherein the method comprises
a) preparing a precipitation mixture by adding at least one disruption reagent, at least one metal cation precipitant and at least one organic solvent selected from aprotic polar solvents and protic solvents to the sample to disrupt the sample and prepare a precipitation mixture which
 i) comprises the metal cation precipitant;
 ii) comprises the organic solvent in a concentration of 15% or less;
 iii) comprises at least one buffering agent;
 iv) has an acidic pH value; and
 v) comprises the disruption reagent,
and precipitating proteins in the sample;
b) separating the precipitate from the supernatant, wherein the supernatant comprises small RNA having a length of less than 200 nt and large RNA having a length of at least 1000 nt; and
c) isolating a nucleic acid from the supernatant.

14. The method according to claim 13, wherein the precipitation mixture comprises the organic solvent in a concentration of 2% to 15% and wherein the organic solvent is water-miscible.

15. The method according to claim 1, having one or more of the following characteristics:
 i) total RNA is isolated from the supernatant;
 ii) small RNA is isolated in form of an enriched fraction;
 iii) the supernatant comprising small RNA and large RNA additionally comprises genomic DNA;
 iv) total nucleic acids are isolated from the supernatant;
 v) genomic DNA is isolated separately from RNA from the supernatant; and/or
 vi) in step c), RNA is bound to a nucleic acid binding solid phase which is a silicon containing a material selected from the group consisting of silica, a polysilicic acid material, a borosilicate, a silicate or glass.

16. The method according to claim 1, for isolating RNA, wherein the method comprises the following steps
 x) disrupting the sample;
 a) preparing a precipitation mixture by adding at least one metal cation precipitant and at least one organic solvent selected from aprotic polar solvents and protic solvents to the disrupted sample, wherein in case a protic solvent is used the protic solvent is a water-miscible alcohol, and wherein the precipitation mixture
  i) comprises the metal cation precipitant in a concentration selected from 300 mM to 625 mM, 350 mM to 600 mM or 400 mM to 550 mM;
  ii) comprises the organic solvent in a concentration selected from 6.5% to 14.5%, 7% to 14%, 8% to 13.5%, 9% to 13% or 9.5% to 12%;
  iii) comprises at least one buffering agent; and
  iv) has an acidic pH value that lies in the range of 3 to 5.25, 3 to 5, 3.25 to 4.75, 3.5 to 4.5 or 3.75 to 4.4,
 and precipitating proteins in the sample;
 b) separating the precipitate from the supernatant, wherein the supernatant comprises small RNA having a length of less than 200 nt and large RNA having a length of at least 1000 nt; and
 c) isolating at least small and large RNA from the supernatant, wherein step c) comprises:
  aa) adding at least one alcohol to the supernatant to provide a binding mixture which comprises the alcohol in a concentration ≥40%, ≥45% or ≥50%;
  bb) binding total RNA contained in the binding mixture to a silicon containing nucleic acid binding solid phase, wherein after step bb), at least large and small RNA is bound to the solid phase;
  cc) optionally washing the bound RNA;
  dd) eluting RNA from the solid phase.

17. A phenol-free method for isolating a nucleic acid from a sample, said method comprising the following steps:
 a) preparing a precipitation mixture comprising a precipitation buffer comprising:
  i) at least one metal cation protein precipitant;
  ii) at least one organic solvent selected from aprotic polar solvents and protic solvents; and
  iii) at least one buffering agent;
 wherein the precipitation buffer has a pH value that lies in a range of 3 to 5.5;
 b) adding said precipitation mixture to said sample to precipitate proteins in the sample;
 c) separating the precipitate from the supernatant, wherein the supernatant comprises small RNA having a length of less than 200 nt and large RNA having a length of at least 1000 nt; and
 d) isolating a nucleic acid from the supernatant.

* * * * *